(12) United States Patent
Schabbach et al.

(10) Patent No.: US 11,931,557 B2
(45) Date of Patent: Mar. 19, 2024

(54) DOSAGE MEASUREMENT SYSTEM

(71) Applicant: SANOFI, Paris (FR)

(72) Inventors: Michael Schabbach, Frankfurt am Main (DE); Michael Jugl, Frankfurt am Main (DE)

(73) Assignee: Sanofi, Paris (FR)

( * ) Notice: Subject to any disclaimer, the term of this patent is extended or adjusted under 35 U.S.C. 154(b) by 714 days.

(21) Appl. No.: 16/957,214

(22) PCT Filed: Dec. 20, 2018

(86) PCT No.: PCT/EP2018/086103
§ 371 (c)(1),
(2) Date: Jun. 23, 2020

(87) PCT Pub. No.: WO2019/129622
PCT Pub. Date: Jul. 4, 2019

(65) Prior Publication Data
US 2020/0405970 A1 Dec. 31, 2020

(30) Foreign Application Priority Data
Dec. 28, 2017 (EP) .................................... 17306954

(51) Int. Cl.
*A61M 5/315* (2006.01)
*A61M 5/20* (2006.01)
*A61M 5/31* (2006.01)

(52) U.S. Cl.
CPC .... *A61M 5/31568* (2013.01); *A61M 5/31585* (2013.01); *A61M 5/20* (2013.01);
(Continued)

(58) Field of Classification Search
CPC ...... A61M 5/31568; A61M 2005/3126; A61M 2205/3306
See application file for complete search history.

(56) References Cited

U.S. PATENT DOCUMENTS

| 2016/0287807 A1 | 10/2016 | Madsen et al. |
| 2017/0151392 A1 | 6/2017 | Marsh et al. |

(Continued)

FOREIGN PATENT DOCUMENTS

| CN | 103702699 | 4/2014 |
| CN | 105764550 | 7/2016 |

(Continued)

OTHER PUBLICATIONS

PCT International Preliminary Report on Patentability in International Appln. No. PCT/EP2018/086103, dated Jun. 30, 2020, 10 pages.

(Continued)

*Primary Examiner* — Dung T Ulsh
(74) *Attorney, Agent, or Firm* — Fish & Richardson P.C.

(57) ABSTRACT

The present disclosure relates to a dosage measurement system for a medicament delivery device. The medicament delivery device comprises a medicament reservoir, a lead screw and a drive sleeve. The drive sleeve is rotatable to axially displace the lead screw relative to the drive sleeve to dispense medicament from the medicament reservoir. The dosage measurement system comprises a sensor unit and a processor. The sensor unit is configured to measure rotation of at least one of the drive sleeve and lead screw. The processor is configured to determine a dosage dispensed from the medicament reservoir based on the measured rotation of said at least one of the drive sleeve and lead screw.

18 Claims, 12 Drawing Sheets

(52) U.S. Cl.
CPC .............. *A61M 2005/3126* (2013.01); *A61M 2205/3306* (2013.01); *A61M 2205/52* (2013.01); *A61M 2205/581* (2013.01); *A61M 2205/582* (2013.01); *A61M 2205/583* (2013.01); *A61M 2205/8206* (2013.01)

(56) References Cited

U.S. PATENT DOCUMENTS

| | | | |
|---|---|---|---|
| 2017/0232203 | A1 | 8/2017 | Krusell |
| 2017/0304549 | A1 | 10/2017 | Kunz et al. |
| 2019/0275254 | A1* | 9/2019 | Klitmose .......... A61M 5/31553 |

FOREIGN PATENT DOCUMENTS

| | | | |
|---|---|---|---|
| CN | 106456885 | 2/2017 | |
| CN | 106659848 | 5/2017 | |
| CN | 106714878 | 5/2017 | |
| CN | 107405449 | 11/2017 | |
| EP | 3058970 | 8/2016 | |
| EP | 3058970 A1 * | 8/2016 | .............. A61M 5/20 |
| EP | 3184134 | 6/2017 | |
| JP | 2014-520584 | 8/2014 | |
| WO | WO 2013/004844 | 1/2013 | |
| WO | WO 20150/75136 | 5/2015 | |
| WO | WO 2015/138093 | 9/2015 | |
| WO | WO 2016/001300 | 1/2016 | |
| WO | WO 2016/050902 | 4/2016 | |
| WO | WO 2016/113348 | 7/2016 | |
| WO | WO 2016/142511 | 9/2016 | |

OTHER PUBLICATIONS

PCT International Search Report and Written Opinion in International Appln. No. PCT/EP2018/086103, dated Mar. 4, 2019, 15 pages.

* cited by examiner

DOSAGE MEASUREMENT SYSTEM

CROSS REFERENCE TO RELATED APPLICATIONS

The present application is the national stage entry of International Patent Application No. PCT/EP2018/086103, filed on Dec. 20, 2018, and claims priority to Application No. EP 17306954.3, filed on Dec. 28, 2017, the disclosures of which are incorporated herein by reference.

TECHNICAL FIELD

The present disclosure relates to a dosage measurement system. The present disclosure also relates to a dosage measurement device, a medicament delivery system, and to a method of determining a dosage of medicament dispensed from a medicament delivery device.

BACKGROUND

A variety of diseases exists that require regular treatment by injection of a medicament. Such injection can be performed by using injection devices, which are applied either by medical personnel or by patients themselves. As an example, type-1 and type-2 diabetes can be treated by patients themselves by injection of insulin doses, for example once or several times per day. For instance, a pre-filled disposable insulin pen can be used as an injection device. Alternatively, a re-usable pen may be used. A re-usable pen allows replacement of an empty medicament cartridge by a new one. Either pen may come with a set of one-way needles that are replaced before each use. The insulin dose to be injected can then for instance be manually selected at the insulin pen by turning a dosage knob and observing the actual dose from a dose window or display of the insulin pen. The dose is then injected by inserting the needle into a suited skin portion and pressing an injection button of the insulin pen. To be able to monitor insulin injection, for instance to prevent false handling of the insulin pen or to keep track of the doses already applied, it is desirable to measure information related to a condition and/or use of the injection device, such as for instance information on the injected insulin dose.

SUMMARY

It is an object of the present disclosure to provide an improved dosage measurement system, dosage measurement device, medicament delivery system, and method of determining a dosage of medicament dispensed from a medicament delivery device.

According to the present disclosure, there is provided a dosage measurement system for a medicament delivery device, wherein the medicament delivery device comprises a medicament reservoir, a lead screw and a drive sleeve that is rotatable to axially displace the lead screw relative to the drive sleeve to dispense medicament from the medicament reservoir, the dosage measurement system comprising: a sensor unit configured to measure rotation of at least one of the drive sleeve and lead screw; and, a processor configured to determine a dosage dispensed from the medicament reservoir based on the measured rotation of said at least one of the drive sleeve and lead screw.

In some embodiments, the sensor unit may be attached to the end of an existing medicament delivery device without requiring major modification of the medicament delivery device. For instance, the sensor unit may be attached to, for example, the proximal end of the medicament delivery device to measure the rotation of the lead screw or drive sleeve.

In one embodiment, the sensor unit is configured to be at least partially located within the drive sleeve. This helps to reduce the size of the medicament delivery device.

In one embodiment, the sensor unit is configured to transmit a signal such that said signal is reflected from said at least one of the drive sleeve and lead screw, the sensor unit configured to receive said reflected signal. The sensor unit may comprise a transmission member, said signal being transmitted through the transmission member. Thus, the transmission member helps to direct the signal towards the dispensing member. Therefore, the sensor itself does not need to be positioned in proximity to the dispensing member. The transmission member may comprise a light guide. In one embodiment, the transmission member extends into the drive sleeve.

In one embodiment, the dosage measurement system comprises a first part configured to be fixed to a medicament delivery device and a second part that is removably attachable to the first part and, preferably, wherein the second part comprises the processor. Thus, the first part may be disposed of with the medicament delivery device and the second part may be attached to the first part of a further medicament delivery device and re-used. In one embodiment, the first part comprises the transmission member. Thus, the second part may be removably attachable to the first part comprising the transmission member.

In one embodiment, the drive sleeve engages the lead screw. In one embodiment, the lead screw is at least partially within the drive sleeve.

In one embodiment, the sensor unit is configured to transmit a signal that travels within the drive sleeve and is reflected from said at least one of the drive sleeve and lead screw.

In one embodiment, the sensor unit is configured such that the signal is reflected from a radially-inwardly facing surface of the drive sleeve.

In one embodiment, said at least one of the drive sleeve and lead screw comprises one or more detection elements that are detectable by the sensor unit.

In one embodiment, the sensor unit is integrated with the medicament delivery device.

In one embodiment, the sensor unit is removably attachable to the medicament delivery device. Therefore, the medicament delivery device can be disposed of and the sensor unit detached from the medicament delivery device for re-use prior to disposal of the medicament delivery device.

In one embodiment, the sensor unit comprises at least one of an optical sensor, magnetic sensor or capacitive sensor.

In one embodiment, the dosage measurement system comprises a display. The display may be configured to display dosage information.

In one embodiment, the medicament delivery device comprises an actuator that is actuatable by a user to dispense medicament, and wherein the sensor unit is configured to be mounted to the actuator. The actuator may comprise a space, and the sensor unit may be configured to be at least partially received in the space.

In one embodiment, the sensor unit is configured to measure rotation of the drive sleeve and the processor is configured to determine a dosage dispensed from the medicament reservoir based on the measured rotation of the drive sleeve. The sensor unit may be configured such that said signal is reflected from a radially-inwardly facing surface of the drive sleeve. In another embodiment, the sensor unit is configured to measure rotation of the lead screw and the processor is configured to determine a dosage dispensed from the medicament reservoir based on the measured rotation of the lead screw.

According to the present disclosure there is also provided a dosage measurement device comprising a dosage measurement system according to the disclosure.

According to the present disclosure, there is also provided a medicament delivery system comprising: a medicament delivery device comprising a medicament reservoir, a lead screw and a drive sleeve that is rotatable to axially displace the lead screw relative to the drive sleeve to dispense medicament from the medicament reservoir; and, a dosage measurement system according to the disclosure. In one embodiment, the medicament reservoir contains medicament.

According to the present disclosure, there is provided a method of determining a dosage of medicament dispensed from a medicament delivery device, wherein the medicament delivery device comprises a medicament reservoir, a lead screw and a drive sleeve that is rotatable to axially displace the lead screw relative to the drive sleeve to dispense medicament from the medicament reservoir, the method comprising: measuring the rotation of at least one of the drive sleeve and lead screw during the dispensing of medicament from the medicament reservoir; and, determining the dosage dispensed from the medicament reservoir based on the measured rotation of said at least one of the drive sleeve and lead screw.

In one embodiment, measuring the rotation of at least one of the drive sleeve and lead screw during the dispensing of medicament from the medicament reservoir comprises transmitting a signal that travels within the drive sleeve and is reflected from said at least one of the drive sleeve and lead screw.

These and other aspects of the disclosure will be apparent from and elucidated with reference to the embodiments described hereinafter.

BRIEF DESCRIPTION OF THE FIGURES

Embodiments of the disclosure will now be described, by way of example only, with reference to the accompanying drawings, in which.

DETAILED DESCRIPTION

Figure 1:
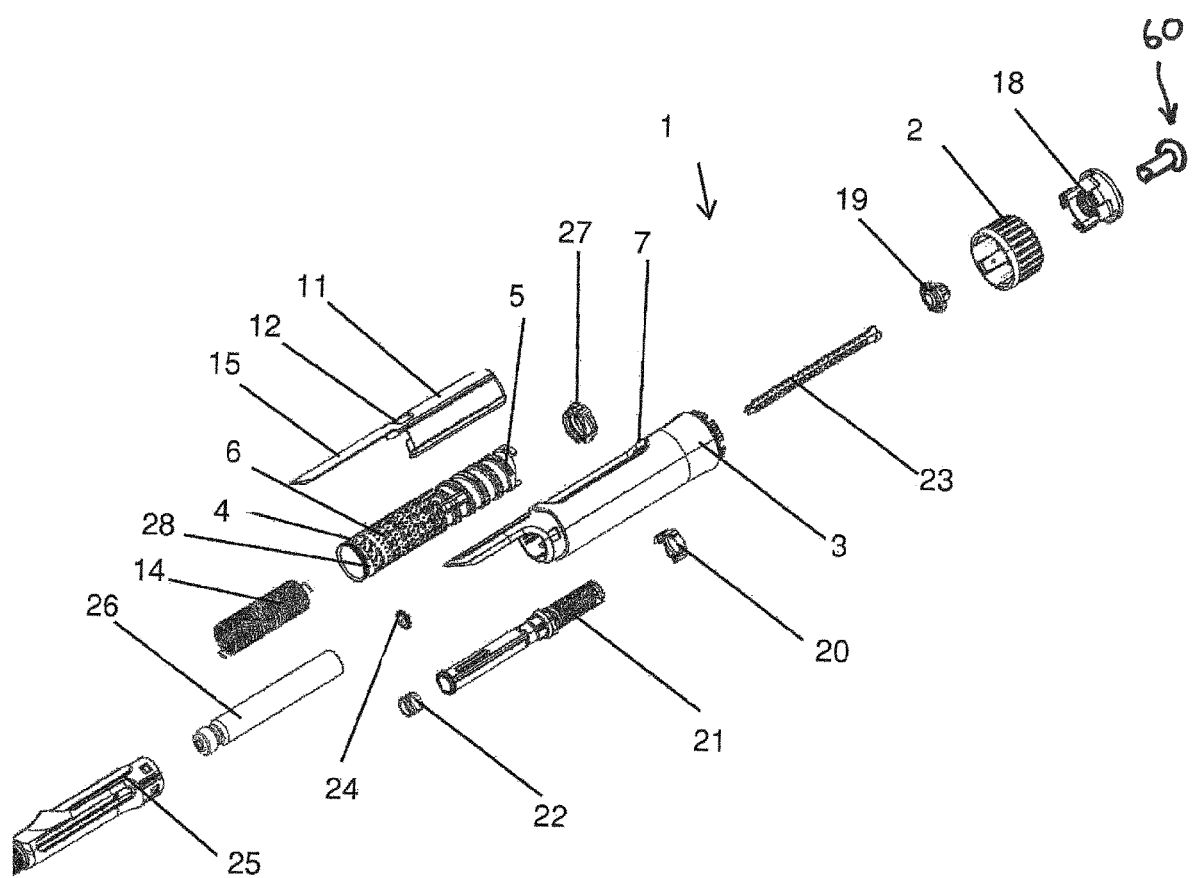
FIG. 1 is an exploded view of a medicament delivery system according to a first embodiment of the disclosure, comprising an injection device and a dosage measurement system.

A drug delivery device, as described herein, may be configured to inject a medicament into a patient. For example, delivery could be sub-cutaneous, intra-muscular, or intravenous. Such a device could be operated by a patient or care-giver, such as a nurse or physician, and can include various types of safety syringe, pen-injector, or auto-injector. The device can include a cartridge-based system that requires piercing a sealed ampule before use. Volumes of medicament delivered with these various devices can range from about 0.5 ml to about 2 ml. Yet another device can include a large volume device ("LVD") or patch pump, configured to adhere to a patient's skin for a period of time (e.g., about 5, 15, 30, 60, or 120 minutes) to deliver a "large" volume of medicament (typically about 2 ml to about 10 ml).

In combination with a specific medicament, the presently described devices may also be customized in order to operate within required specifications. For example, the device may be customized to inject a medicament within a certain time period (e.g., about 3 to about 20 seconds for auto-injectors, and about 10 minutes to about 60 minutes for an LVD). Other specifications can include a low or minimal level of discomfort, or to certain conditions related to human factors, shelf-life, expiry, biocompatibility, environmental considerations, etc. Such variations can arise due to various factors, such as, for example, a drug ranging in viscosity from about 3 cP to about 50 cP. Consequently, a drug delivery device will often include a hollow needle ranging from about 25 to about 31 Gauge in size. Common sizes are 17 and 29 Gauge.

The delivery devices described herein can also include one or more automated functions. For example, one or more of needle insertion, medicament injection, and needle retraction can be automated. Energy for one or more automation steps can be provided by one or more energy sources. Energy sources can include, for example, mechanical, pneumatic, chemical, or electrical energy. For example, mechanical energy sources can include springs, levers, elastomers, or other mechanical mechanisms to store or release energy. One or more energy sources can be combined into a single device. Devices can further include gears, valves, or other mechanisms to convert energy into movement of one or more components of a device.

The one or more automated functions of an auto-injector may each be activated via an activation mechanism. Such an activation mechanism can include an actuator, for example, one or more of a button, a lever, a needle sleeve, or other activation component. Activation of an automated function may be a one-step or multi-step process. That is, a user may need to activate one or more activation components in order to cause the automated function. For example, in a one-step process, a user may depress a needle sleeve against their body in order to cause injection of a medicament. Other devices may require a multi-step activation of an automated function. For example, a user may be required to depress a button and retract a needle shield in order to cause injection.

In addition, activation of one automated function may activate one or more subsequent automated functions, thereby forming an activation sequence. For example, activation of a first automated function may activate at least two of needle insertion, medicament injection, and needle retraction. Some devices may also require a specific sequence of steps to cause the one or more automated functions to occur. Other devices may operate with a sequence of independent steps.

Some delivery devices can include one or more functions of a safety syringe, pen-injector, or auto-injector. For example, a delivery device could include a mechanical energy source configured to automatically inject a medicament (as typically found in an auto-injector) and a dose setting mechanism (as typically found in a pen-injector).

The term "distal" refers to a location that is relatively closer to a site of injection, and the term "proximal" refers to a location that is relatively further away from the injection site.

FIG. 1 is an exploded view of the components of a first embodiment of medicament delivery system comprising a medicament delivery device 1 and a dosage measurement system 60.

In the present embodiment, the medicament delivery device 1 is in the form of an injection device 1. The injection device 1 comprises a dose dial 2 in the form of a dial grip 2, a body or housing 3 with an elongated window 7, and a dose scale drum in the form of a number sleeve 4.

The number sleeve 4 has an outer thread 5 on its outer peripheral surface extending in a helical pattern from a distal end to a proximal end. The number sleeve 4 carries indicia 6 which are printed on the number sleeve. The indicia 6 are on the number sleeve 4 in a helical pattern.

The injection device 1 further comprises a sliding element 11 configured as a gauge component with a sliding window 12.

The injection device 1 further comprises a drive spring 14 in the form of a torsion spring 14, a trigger button 18, a clutch plate 19, a last dose nut 20, a drive sleeve 21, a clutch spring 22, a lead screw 23, and a bearing 24 provided at a distal end of the lead screw 23

A cartridge holder 25 is provided that can be attached to the distal end of the housing 3 and that receives a cartridge 26 which is filled with a medicament and which has a bung (not shown) located inside the cartridge 26. When the bearing 24 is moved in the distal direction, the bearing 24 displaces the bung such that medicament is dispensed from the cartridge 26 when a dispense interface such as a double ended needle cannula is attached to the distal end of the cartridge 26.

The number sleeve 4 comprises an upper number sleeve part 27 referred to a number sleeve upper 27 and a lower number sleeve part 28 referred to as number sleeve lower 28. The dose dial 2 and the button 18 are separate individual components. In the present embodiment, all components are located concentrically about a common principal longitudinal axis of the mechanism. The body or housing 3 may also be a body element that it fixed to an outer housing or casing.

The button 18 is permanently splined to the dose dial 2. It is also splined to the number sleeve upper 28 when the button 18 is not pressed, but this spline interface is disconnected when the button 18 is pressed. When the button 18 is pressed, splines on the button 18 engage with splines on the housing 3 preventing rotation of the button 18 (and hence the dose dial 2) during dispense. These splines disengage when the button 18 is released, allowing a dose to be dialled.

The dose dial 2 is axially constrained to the housing 3. It is rotationally constrained, via the splined interface to the button 18. The number sleeve lower 28 is rigidly fixed to the number sleeve upper 27 during assembly to form the number sleeve 4 and is a separate component to simplify number sleeve 4 mould tooling and assembly. This sub assembly is constrained to the housing 3 by holding elements (not shown) towards the distal end to allow rotation but not translation. The number sleeve lower 28 is marked with indices in the form of a sequence of numbers, which are visible through the window 12 of the sliding element 11 and the window 7 in the housing 3 to denote the dialled dose of medicament.

The clutch plate 19 is splined to the number sleeve 4. It is also coupled to the drive sleeve 21 via a ratchet interface. The ratchet provides a detented position between the number sleeve 4 and the drive sleeve 21 corresponding to each dose unit and engages different ramped tooth angles during clockwise and anti-clockwise relative rotation. The sliding element 11 is constrained to prevent rotation but allow translation relative to the housing 3 via a splined interface. The sliding element 11 has a helical feature on its inner surface which engages with the helical outer thread 5 cut in the number sleeve 4 such that rotation of the number sleeve 4 causes axial translation of the sliding element 11. This helical feature on the sliding element 11 also creates stop abutments against the end of the helical cut in the number sleeve 4 to limit the minimum and maximum dose that can be set.

The last dose nut 20 is located between the number sleeve 4 and the drive sleeve 21. It is rotationally constrained to the number sleeve 4 via a splined interface. It moves along a helical path relative to the drive sleeve 21 via a threaded interface when relative rotation occurs between the number sleeve 4 and drive sleeve 21. The drive sleeve 21 extends from the interface with the clutch plate 19 to the contact with the clutch spring 22. A splined tooth interface with the number sleeve 4 is not engaged during dialling, but engages when the button 18 is pressed, preventing relative rotation between the drive sleeve 21 and number sleeve 4 during dispense.

A further splined tooth interface with the housing 3 prevents rotation of the drive sleeve 21 during dose setting. When the button 18 is pressed, the drive sleeve 21 and the housing 3 disengage allowing the drive sleeve 21 to rotate. The helical drive spring 14 is charged and stores energy during dose setting by the action of the user rotating the dose dial 2. The spring energy is stored until the mechanism is triggered for dispense at which point the energy stored is used to deliver the medicament from the cartridge to the user. The drive spring 14 is attached at one end to the housing 3 and at the other end to the number sleeve 4. The drive spring 14 is pre-wound upon assembly, such that it applies a torque to the number sleeve 4 when the mechanism is at zero units dialled. The action of rotating the dose dial 2 to set a dose rotates the number sleeve 4 relative to the housing 3 and charges the drive spring 14 further.

The lead screw 23 is rotationally constrained to the drive sleeve 21 via a splined interface. When rotated, the lead screw 23 is forced to move axially relative to the drive sleeve 21, through a threaded interface (not shown) with the housing 3. The bearing 24 is axially constrained to the lead screw 23 and acts on the bung within the liquid medicament cartridge 26.

The axial position of the drive sleeve 21, clutch plate 19 and button 18 is defined by the action of the clutch spring 22, which applies a force on the drive sleeve 21 in the proximal direction. This spring force is reacted via the drive sleeve 21, clutch plate 19 and button 18, and when 'at rest' it is further reacted through the dose dial 2 to the housing 3. The spring force ensures that the ratchet interface is always engaged. In the 'at rest' position, it also ensures that the button splines are engaged with the number sleeve 4 and that the drive sleeve teeth are engaged with the housing 3. The housing 3 provides location for the liquid medication cartridge 26 and cartridge holder 25, windows for viewing the dose number and the sliding element, and a feature on its external surface to axially retain the dose dial 2 (not shown). A removable cap fits over the cartridge holder 25 and is retained via clip features on the housing 3.

Figure 2:
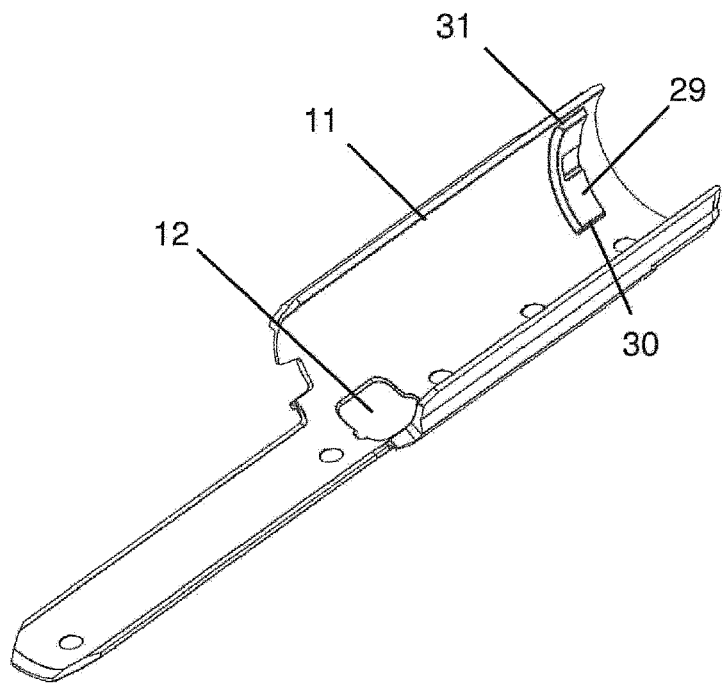
FIG. 2 is a perspective view of a sliding element of the injection device of FIG. 1.
Figure 3:
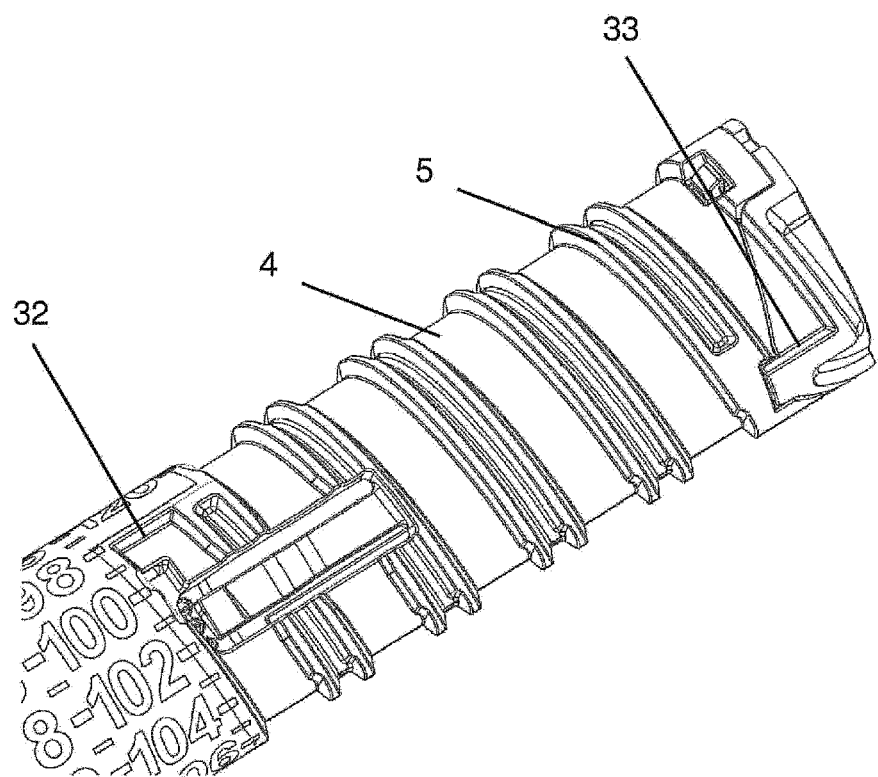
FIG. 3 is a perspective view of a number sleeve of the injection device of FIG. 1.

FIG. 2 shows the inside of the sliding element 11 with the window 12 and a male thread feature 29 on the inner surface of the sliding element 11 that engages the outer thread 5 on the number sleeve 4 (see FIG. 3). The thread feature 29 has a zero dose abutment 30 and a maximum dose abutment 31. As shown in FIG. 3, the outer thread 5 has a zero dose abutment 32 at one end of the thread 5 and a maximum dose abutment 33 at the other end of the outer thread 5 so that any dose size can be selected between zero and a pre-defined maximum, in increments to suit the medicament and user profile. The drive spring 14, which has a number of pre-wound turns applied to it during assembly of the device, applies a torque to the number sleeve 4 and is prevented from rotating by the zero dose abutment.

Figure 4:
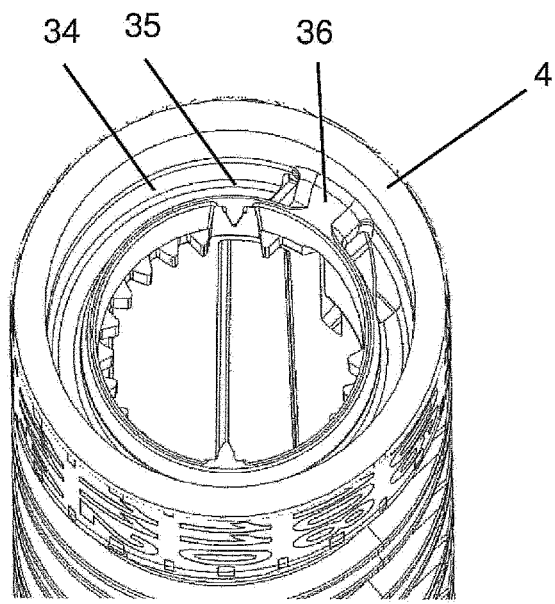
FIG. 4 is a perspective view of another section of the number sleeve of FIG. 3.

As shown in FIG. 4, the inner surface of the number sleeve 4 has a lead-in 34 followed by a groove 35 and an anchor point 36. Automated assembly of the drive spring 14 into the number sleeve may be achieved by incorporating the large lead-in 34 and the groove feature 35. As the drive spring 14 is rotated during assembly, a hook end 37 at the one end of the drive spring 14 (see FIG. 5) locates in the groove feature 35 before engaging the anchor point 36 in the number sleeve 4.

Figure 5:
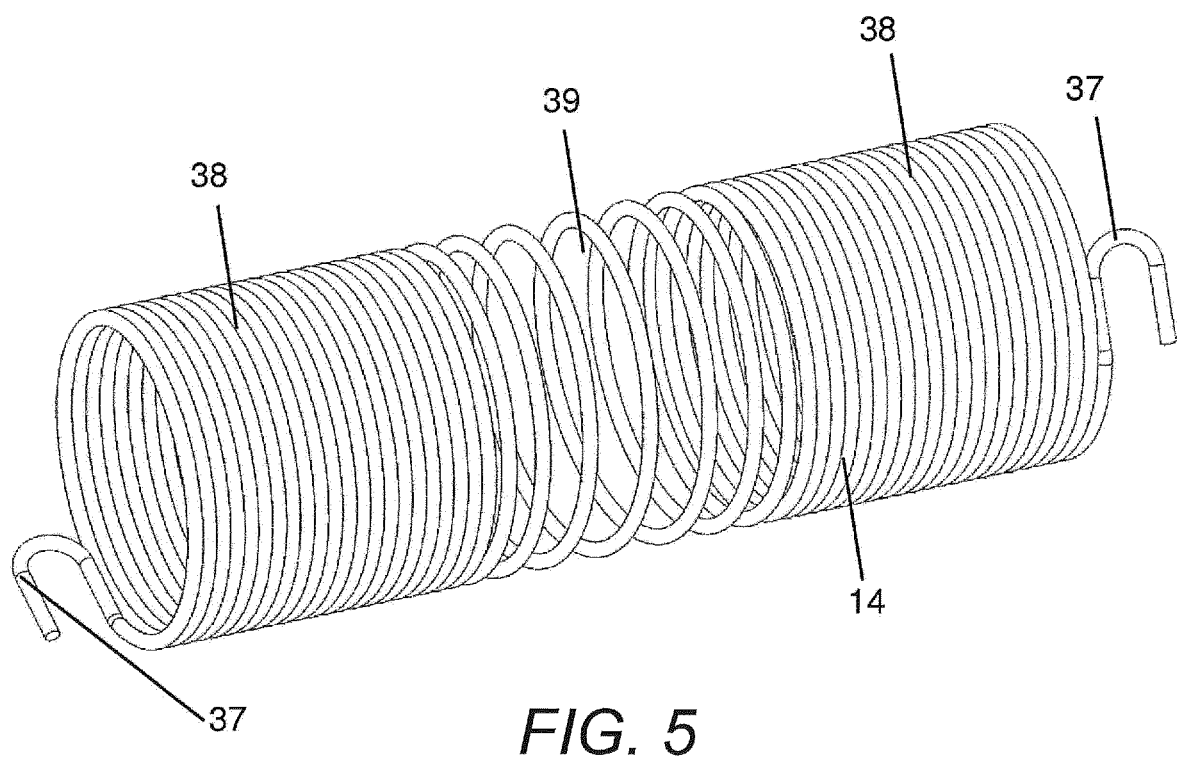
FIG. 5 is a perspective view of a drive spring of the injection device of FIG. 1.

As shown in FIG. 5, the drive spring 14 is formed from a helical wire with at least two different pitches. Both ends are formed from 'closed' coils 38, i.e. the pitch equals the wire diameter and each coil contacts the adjacent coil. The central portion has 'open' coils 39, i.e. the coils do not contact each other. Following assembly, compression in the drive spring 14 biases the number sleeve 5 axially relative to the housing 3 in a consistent direction, reducing the effects of geometric tolerances.

Figure 6A:
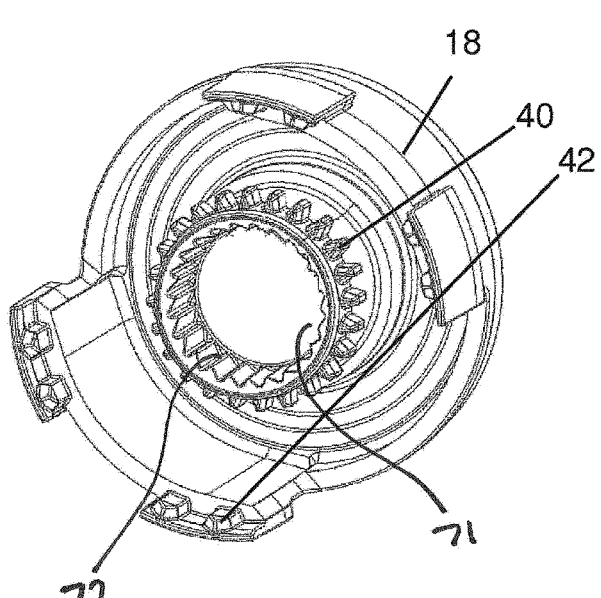
FIG. 6A is a perspective view of a button and the number sleeve of the injection device of FIG. 1.
Figure 6B:
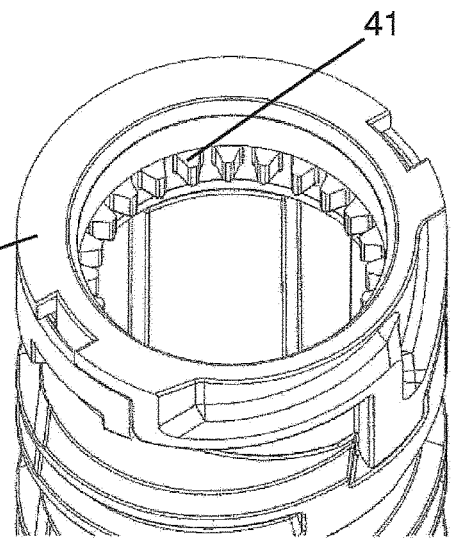
FIG. 6B is another perspective view of the button and number sleeve of the injection device of FIG. 1.

For selecting a dose, the user rotates the dial grip 2 clockwise. As shown in FIGS. 6A and 6B, the button 18 has inner splines 40 for engaging corresponding splines 41 on the upper part of number sleeve 4 to create a splined interface 40/41. The dial grip 2 is splined to the button 18, wherein the button 18 has a further set of splines 42 for engagement with corresponding splines of the housing 3. During dose selection, rotation of the dial grip 2 is transferred to the button 18. The button 18 is in turn splined to the number sleeve upper 27 (during dose selection only) via the splines 40. The number sleeve upper 27 is permanently fixed to the number sleeve lower 28 to form the number sleeve 4. Therefore, rotation of the dial grip 2 generates an identical rotation in the number sleeve 4. Rotation of the number sleeve 4 causes charging of the drive spring 14, increasing the energy stored by the drive spring 14. As the number sleeve 4 rotates, the sliding element 11 translates axially due to its threaded engagement with the number sleeve 4 thereby showing the value of the dialled dose.

Figure 7:
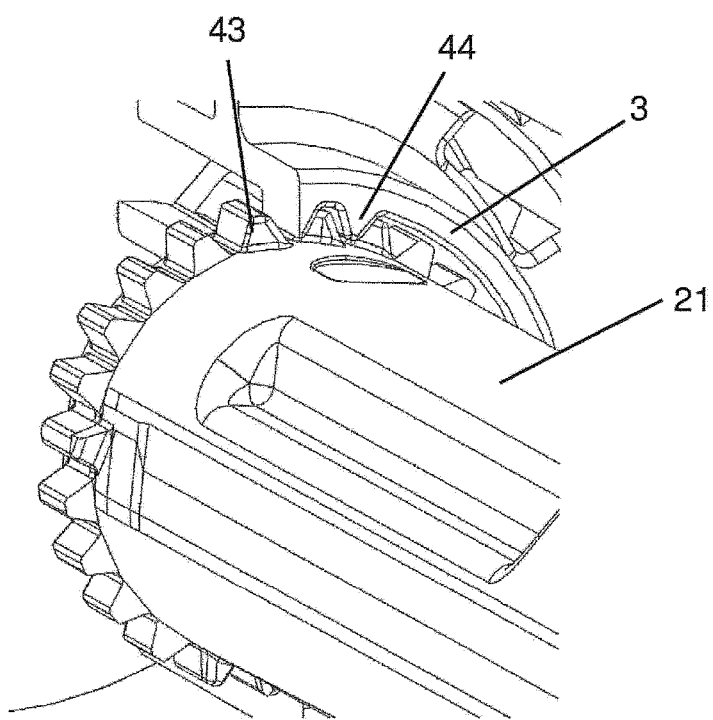
FIG. 7 is a perspective view of parts of the drive mechanism of the injection device of FIG. 1.

As shown in FIG. 7, the drive sleeve 21 has splines 43 for engaging corresponding splines 44 formed on the inside of the housing 3 to create a splined interface 43/44. The drive sleeve 21 is prevented from rotating as the dose is set and the number sleeve 4 is rotated, due to the engagement of its splined teeth 43 with the teeth 44 of the housing 3. Relative rotation therefore occurs between the clutch plate 19 that is driven by the number sleeve 4 and the drive sleeve 21 via the ratchet interface.

Figure 8A:
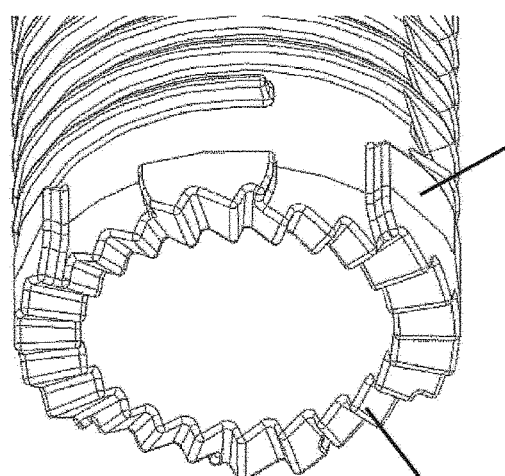
FIG. 8A is a perspective view of a drive sleeve of the injection device of FIG. 1.
Figure 8B:
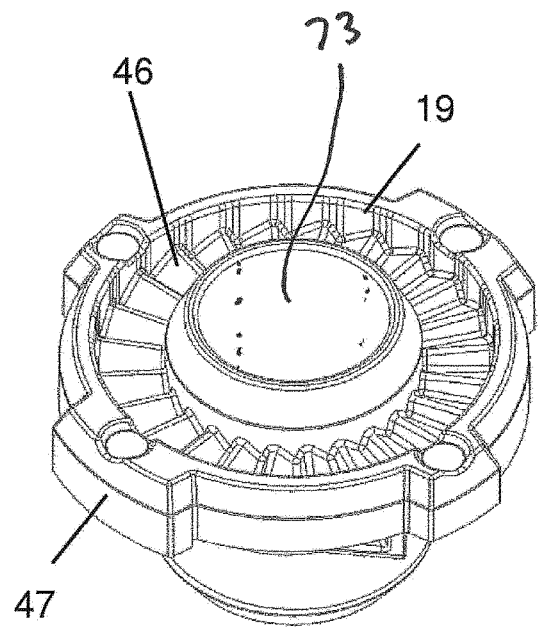
FIG. 8B is a perspective view of a clutch plate of the injection device of FIG. 1.

As shown in FIGS. 8A and 8B, an end surface of the drive sleeve 21 is provided with angled teeth 45 and the clutch plate 19 is provided with angled teeth 46. The angled teeth 45 of the drive sleeve 21 form the ratchet interface 45/46 together with the angled teeth 46 on the clutch plate 19.

On the outer circumference of the clutch plate 19, splined teeth 47 for engaging a corresponding groove on the number sleeve 4 are formed. The user torque required to rotate the dial grip 2 is a sum of the torque required to wind up the drive spring 14, and the torque required to overhaul the ratchet interface 45/46. The clutch spring 22 is designed to provide an axial force to the ratchet interface 45/46 and to bias the clutch plate 19 onto the drive sleeve 21.

This axial load acts to maintain the ratchet teeth 45, 46 engagement of the clutch plate 19 and the drive sleeve 21. The torque required to overhaul the ratchet interface 45/46 in the dose set direction is a function of the axial load applied by the clutch spring 22, the clockwise ramp angle of the ratchet, the friction coefficient between the mating surfaces and the mean radius of the ratchet features. As the user rotates the dial grip 2 sufficiently to increment the mechanism by 1 increment, the number sleeve 14 rotates relative to the drive sleeve 21 by 1 ratchet tooth. At this point the ratchet teeth 45, 46 re-engage into the next detented position. An audible click is generated by the ratchet re-engagement, and tactile feedback is given by the change in torque input required.

With no user torque applied to the dial grip 2, the number sleeve 4 is prevented from rotating back under the torque applied by the drive spring 14, solely by the ratchet engagement 45/46 between the clutch plate 19 and the drive sleeve 21. The torque necessary to overhaul the ratchet interface 45/46 in the anti-clockwise direction is a function of the axial load applied by the clutch spring 22, the anti-clockwise ramp angle of the ratchet teeth 45,46, the friction coefficient between the mating surfaces and the mean radius of the ratchet features. The torque necessary to overhaul the ratchet interface 45/46 must be greater than the torque applied to the number sleeve 4 (and hence clutch plate 19) by the drive spring 14. The ratchet ramp angle is therefore increased in the anticlockwise direction to ensure this is the case whilst ensuring the dial-up torque is as low as possible. The user may choose to increase the selected dose by continuing to rotate the dial grip 2 in the clockwise direction. The process of overhauling the ratchet interfaces 45/46 between the number sleeve 4 and drive sleeve 21 is repeated for each dose increment. Additional energy is stored within the drive spring 14 for each dose increment and audible and tactile feedback is provided for each increment dialled by the re-engagement of the ratchet teeth 45, 46. The torque required to rotate the dial grip 2 increases as the torque required to wind up the drive spring 14 increases. The torque required to overhaul the ratchet interface 45/46 in the anti-clockwise direction must therefore be greater than the torque applied to the number sleeve 4 by the drive spring 14 when the maximum dose has been reached.

If the user continues to increase the selected dose until the maximum dose limit is reached, the number sleeve 4 engages with the maximum dose abutment 31 on the sliding element 11 (see FIGS. 2 and 3. This prevents further rotation of the number sleeve 4, clutch plate 19 and dial grip 2.

The last dose nut 20 is splined to the number sleeve 4 while the last dose nut 20 is threaded to the drive sleeve 21 such that relative rotation of the number sleeve 4 and the drive sleeve 21 during dose setting also causes the last dose nut 20 to travel along its threaded path towards a last dose abutment on the drive sleeve 21. Depending on how many increments have already been delivered by the mechanism, during selection of a dose, the last dose nut 21 may contact its last dose abutment with the drive sleeve 21. The abutment prevents further relative rotation between the number sleeve 4 and the drive sleeve 21 and therefore limits the dose that can be selected. The position of the last dose nut 20 is determined by the total number of relative rotations between the number sleeve 4 and the drive sleeve 21, which have occurred each time the user sets a dose.

When a dose has been set, the user is able to deselect any number of increments from this dose. Deselecting a dose is achieved by the user rotating the dial grip 2 anti-clockwise. The torque applied to the dial grip 2 by the user is sufficient, when combined with the torque applied by the drive spring 14, to overhaul the ratchet interface 45/46 between the clutch plate 19 and the drive sleeve 21 in the anti-clockwise direction. When the ratchet interface 45/46 is overhauled, anti-clockwise rotation occurs in the number sleeve 4 (via the clutch plate 19), which returns the number sleeve 4 towards the zero dose position, and unwinds the drive spring 14. The relative rotation between the number sleeve 4 and drive sleeve 21 causes the last dose nut 20 to return along its helical path, away from the last dose abutment.

Figure 9A:
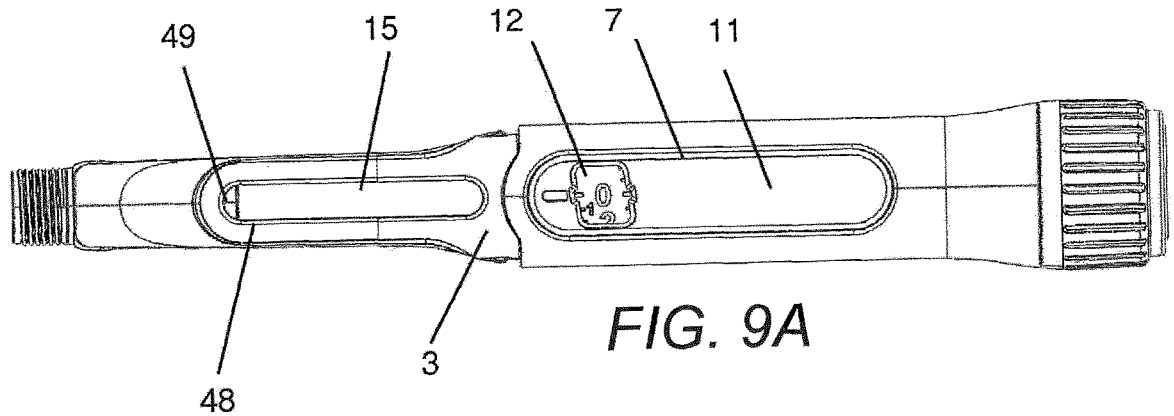
FIGS. 9A and 9B depict a dose setting sequence of the injection device of FIG. 1 in a side view.
Figure 9B:
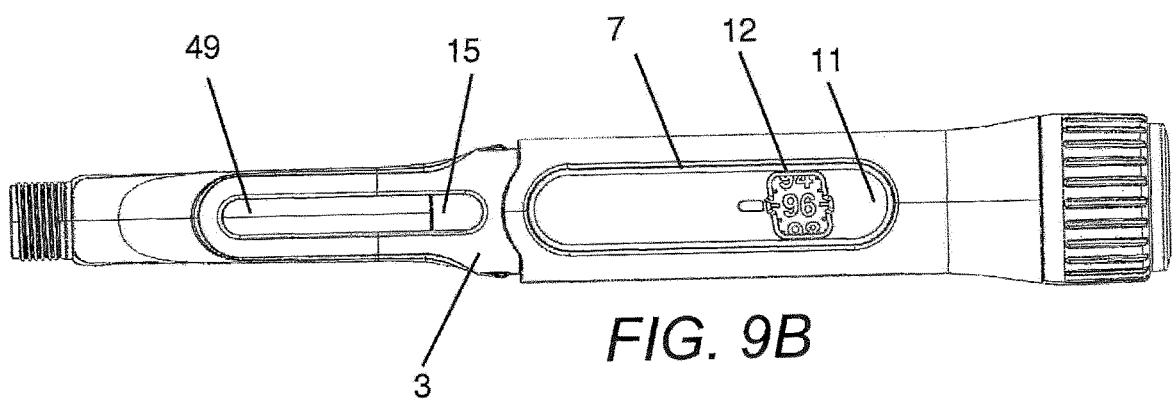

As shown in FIGS. 9A and 9B, the sliding element 11 has flanges or extensions on either side of the window area which cover the numbers printed on the number sleeve 4 adjacent to the dialled dose to ensure only the set dose number is made visible to the user. The injection device 1 includes a visual feedback feature in addition to the discrete dose number display. The distal end of the sliding element 11 has the extension 15 (see FIG. 1) that creates a sliding scale through a window 48 in the housing 3. Window 48 may be smaller than window 7.

As a dose is set by the user, the sliding element 11 translates axially, the distance moved proportional to the magnitude of the dose set. This feature gives clear feedback to the user regarding the approximate size of the dose set. The dispense speed of the injection device 1 may be higher than for a manual injector device, so it may not be possible to read the numerical dose display during dispense. The sliding element 11 provides feedback to the user during dispense regarding dispense progress without the need to read the dose number itself.

The window 48 may be formed by an opaque element on the sliding element 11 revealing a contrasting coloured component 49 underneath. Alternatively, a revealable element 49 may be printed with coarse dose numbers or other indices to provide more precise resolution. In addition, this display simulates a syringe action during dose set and dispense.

To reduce dust ingress and prevent the user from touching moving parts, the viewing openings 7 and 48 in the housing 3 are covered by translucent windows. These windows 7, 48 may be separate components, but in this embodiment they are incorporated into the housing 3 using 'twin-shot' moulding technology. A first shot of translucent material forms the internal features and the windows, and then a 'second shot' of opaque material forms the outer cover of the housing 3.

Delivery of a dose is initiated by the user depressing the button 18 axially. When the button 18 (see FIGS. 6A and 6B) is depressed, the splines 40 and 41 between the button 18 and the number sleeve 4 disengage, rotationally disconnecting the button 18 and dial grip 21 from the delivery mechanism.

Figure 10:
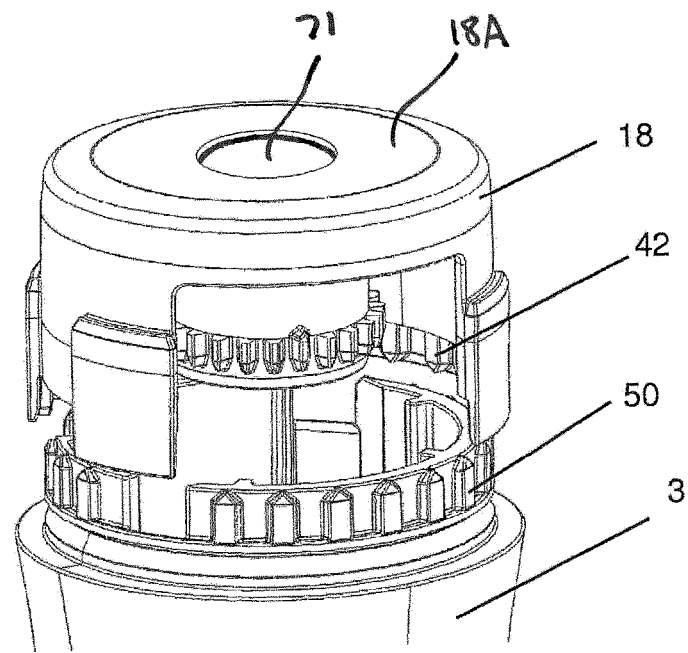
FIG. 10 is a perspective view of the button and a housing of the injection device of FIG. 1.

As shown in FIG. 10, the splines 42 on the button 18 engage with splines 50 on the housing 3 preventing rotation of the button 18 (and hence the dial grip 21) during dispense. As the button 18 is stationary during dispense, it can be used in a dispense clicker mechanism. A stop feature in the housing 3 limits axial travel of the button 18 and reacts any axial abuse loads applied by the user, reducing the risk of damaging internal components.

Figure 11:
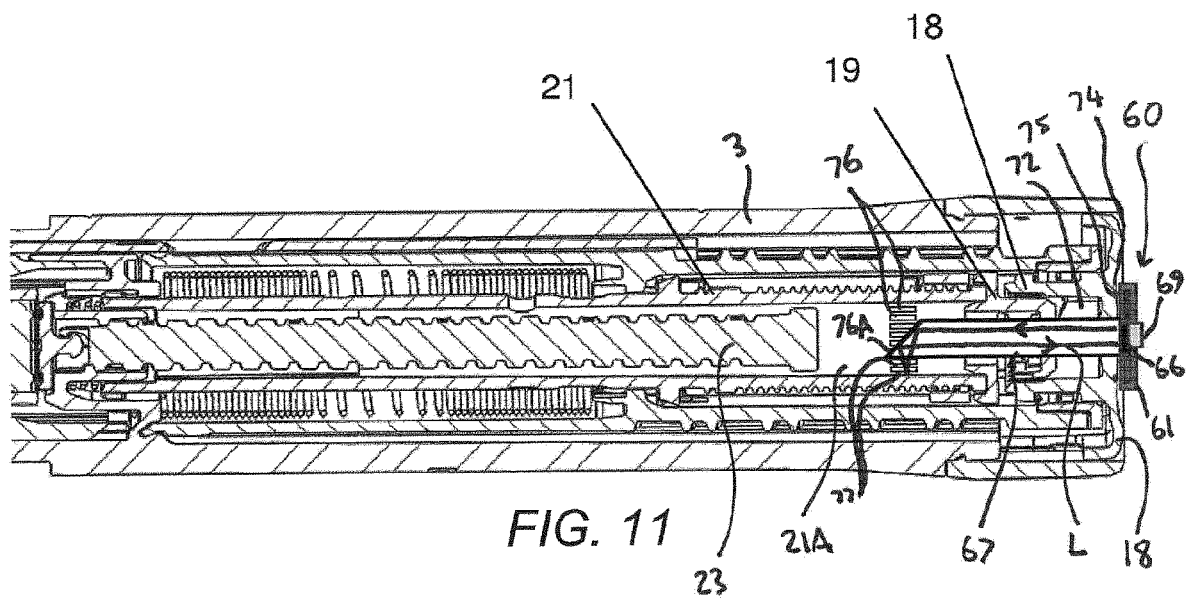
FIG. 11 is a cross-sectional side view of the medicament delivery system of FIG. 1.
Figure 12A:
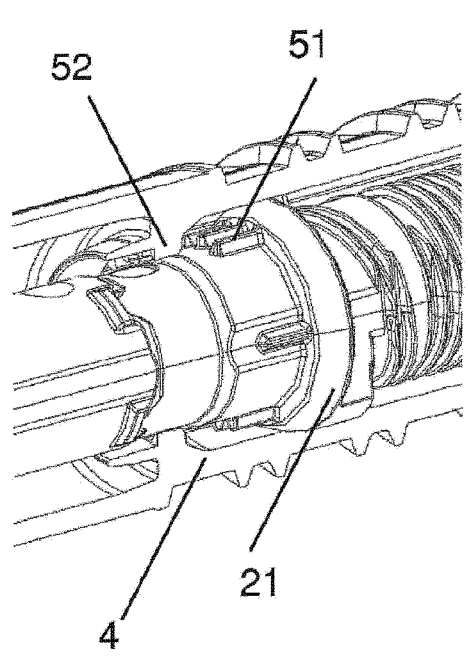
FIGS. 12A and 12B depict an interaction between the drive sleeve and number sleeve of the injection device of FIG. 1.
Figure 12B:
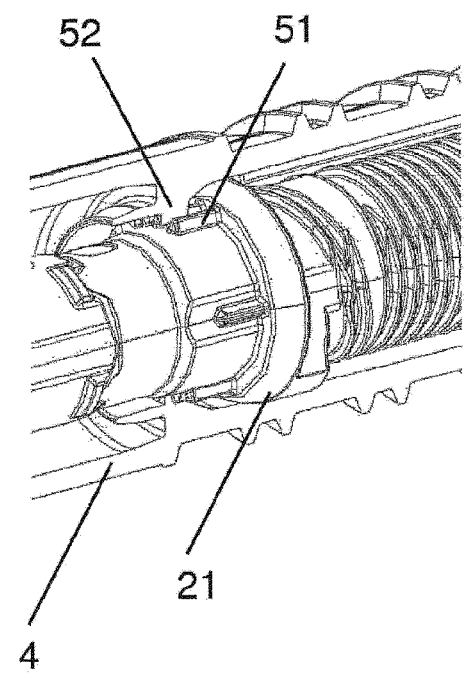
Figure 13:
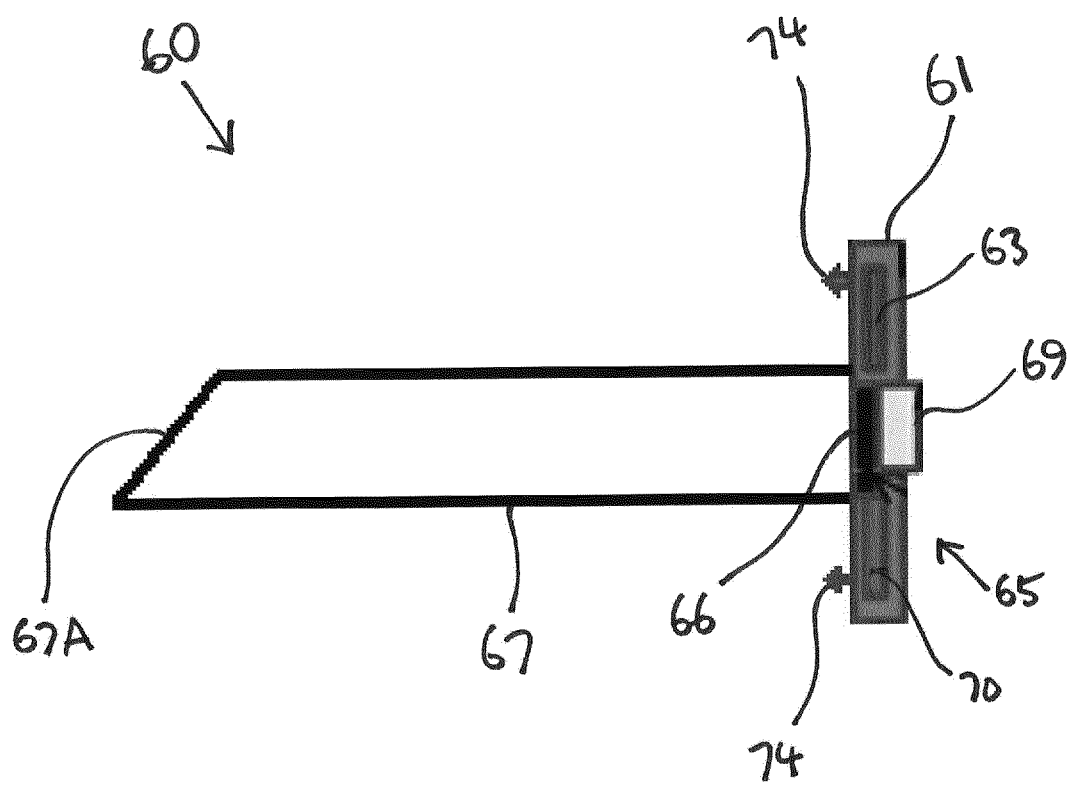
FIG. 13 is a side view of the dosage measurement system of FIG. 1.

As shown in FIG. 11, the clutch plate 19, arranged between the drive sleeve 21 and the button 18, is moved axially by the button 18. Moreover, the drive sleeve 21 is moved axially by the clutch plate 19. As shown in FIGS. 12A and 12B, the axial displacement of the drive sleeve 21 engages splines 51 on the drive sleeve 21 with splines 52 on the number sleeve 4 so that a splined tooth interface 51/52 is formed preventing relative rotation between the drive sleeve 21 and number sleeve 4 during dispense.

The splined tooth interface 43/44 (shown in FIG. 7) between the drive sleeve 21 and the housing 3 disengages, so that the drive sleeve 21 can now rotate relative to the housing 3 and is driven by the drive spring 14 via the number sleeve 4, and clutch plate 19. Rotation of the drive sleeve 21 causes the lead screw 23 to rotate due to their splined engagement, and the lead screw 23 then advances due to its threaded engagement to the housing 3. The number sleeve 4 rotation also causes the sliding element 11 to traverse axially back to its zero position whereby the zero dose abutment (shown in FIGS. 2 and 3) stops the mechanism.

It is possible to angle the spline teeth on either the drive sleeve 21 or the housing 3 so that when the zero dose abutment 30 stops rotation of the number sleeve 4 and hence the drive sleeve 21 at the end of the dose and the button 18 is released, the spline teeth between the drive sleeve 21 and the housing 3 rotate the drive sleeve 21 backwards by a small amount. This moves the lead screw 23 axially back away from the bung and rotates the number sleeve lower 28 from the zero dose stop position, helping to prevent possible weepage.

In the present embodiment, the dosage measurement system 60 is in the form of a dosage measurement device 60 that is attached to a proximal end of the injection device 1.

The dosage measurement device 60 comprises a housing 61 and a display 62 for presenting dosage information.

However, it should be recognised that in alternative embodiments (not shown) the display 62 is omitted.

Figure 14:
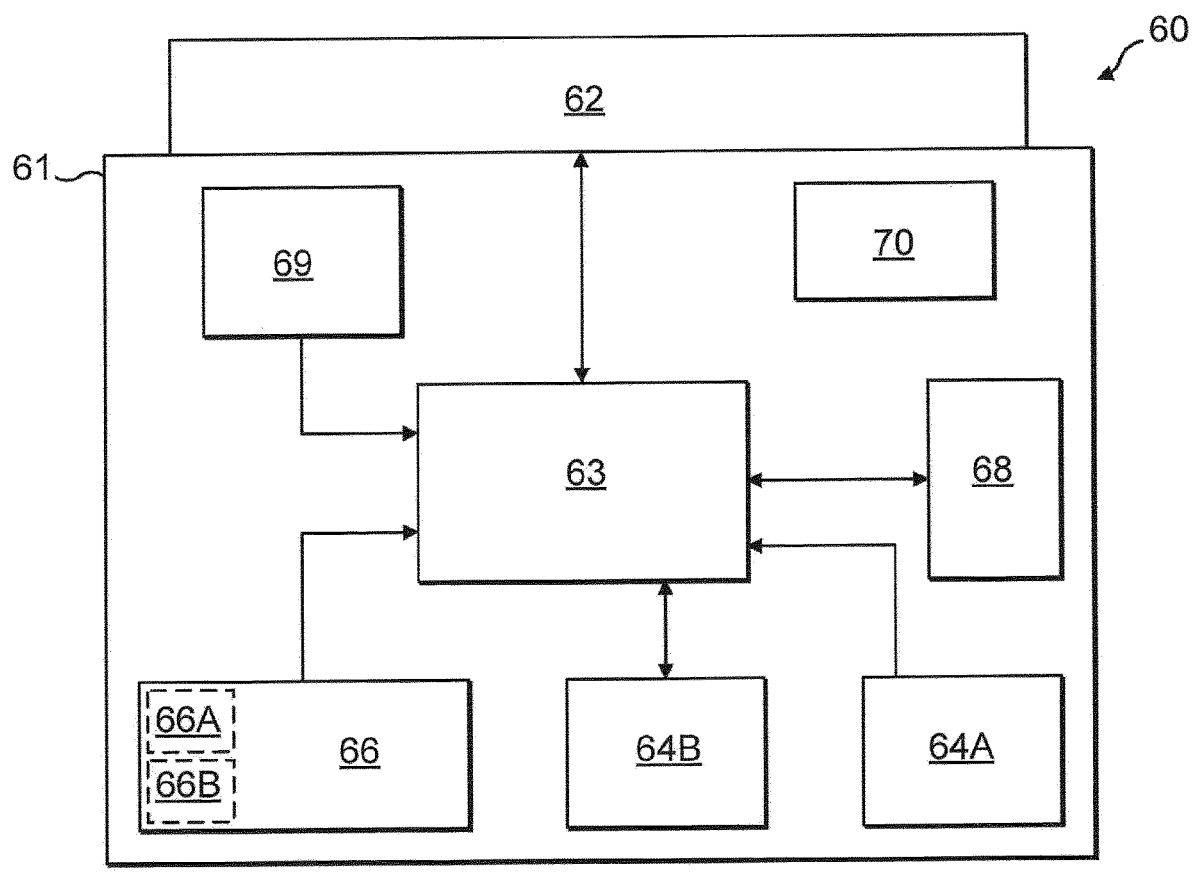
FIG. 14 is a block diagram of the dosage measurement system of FIG. 1.

As shown in FIG. 14, the data measurement device 60 also includes one or more processors 63, such as a microprocessor, a Digital Signal Processor (DSP), Application Specific Integrated Circuit (ASIC), Field Programmable Gate Array (FPGA) or the like, together with one or more computer readable memory media 64. In the present embodiment, the computer readable memory media 64 comprises memory units 64A, 64B, including program memory 64A and main memory 64B, which can store software for execution by the processor 63.

A sensor unit 65, comprising one or more sensors 66, is provided. In this particular example, the sensor 66 comprises an optical sensor 66. More specifically, the optical sensor 66 is in the form of an optical encoder 66. The optical encoder 66 includes a light source 66A, such as a light emitting diode (LED), and a light detector 66B, such as an optical transducer.

The sensor unit 65 further comprises a light guide 67 in the form of an optical prism 67, which is described in more detail below.

The dosage measurement device 60 further comprises an output 68, a power switch 69 and a battery 70. Actuation of the power switch 69 powers the dosage measurement device 60 on and off.

In one embodiment, the power switch 69 comprises a button 69 on the housing 61 of the dosage measurement device 60 that is actuated by the user. In another embodiment, the power switch 69 is configured to respond to pressure applied to the display 62 by powering the dosage measurement device 60 on or off. In yet another embodiment (not shown), the power switch 69 is actuated when the user actuates the button 18. For instance, the power switch 69 may comprise an electrical contact (not shown) on the button 18 that makes electrical contact with a second electrical contact (not shown) on a different part of the injection device 1, for example, the housing 3 or number sleeve 4, when the button 18 is pressed to power the dosage measurement device 60 on. When the first and second electrical contacts make contact, a power circuit may be closed such that the dosage measurement device 60 is powered on. Advantageously, such an arrangement helps to ensure that the dosage measurement device 60 is only operated to measure a dosage being delivered when the button 18 is pressed into the housing 3 and is thus in its operating position. This may improve accuracy of dosage measurement because otherwise movement of the button 18 axially into the housing 3, which moves the sensor unit 65 towards the lead screw 23 and thus reduces the distance 'D' therebetween, may appear to the sensor unit 65 as if the medicament reservoir is being refilled with medicament. Moreover, movement of the button 18 axially out of the housing 3 when the button 18 is released, which moves the sensor unit 65 away the lead screw 23 and thus increases the distance 'D' therebetween, may appear to the sensor unit 65 as if a dosage is being expelled from the injection device 1. However, it should be recognised that other arrangements to help ensure that the dosage measurement device 60 is only operated to measure a dosage being delivered when the button 18 is in its operating position are also possible. For instance, the processor 63 may be configured to only start measuring the dosage dispensed from the injection device 1 once it has calculated that the sensor unit 65 has moved towards the lead screw 23 by a distance D that corresponds to the button 18 being actuated by the user. Additionally, or alternatively, if the processor 63 calculates that the sensor unit 65 has moved relative to the lead screw 23 by a distance D in a time period that is consistent with the button 18 being released, the processor 63 may disregard this dosage measurement or flag it as the button 18 being released. In a yet further embodiment, the power switch 69 is arranged such that pressing the button 18 results in the power switch 69 simultaneously being pressed to power on the dosage measurement device 60 and/or releasing the button 18 results in the power switch 69 being released to power off the dosage measurement device 60.

In the present embodiment, the processor 63, computer readable memory media 64, sensor 66, output 68 and battery 70 are located within the housing 61. However, it should be recognized that in alternative embodiments (not shown) one or more of these components may be located external of the housing 61.

The output 68 may be a wireless communications interface for communicating with another device via a wireless network such as wi-fi or Bluetooth®, or an interface for a wired communications link, such as a socket for receiving a Universal Series Bus (USB), mini-USB or micro-USB connector.

FIG. 11 shows the dosage measurement device 60 and the proximal end of the injection device 1.

The button 18 includes an aperture 71 in its proximal surface 18A, configured such that at least a portion of the dosage measurement device 60 can be received in a space 72 within the button 18. In the present embodiment, the clutch plate 19 comprises an aperture 73 and at least a portion of the data measurement device 60 extends through the aperture 73 in the clutch plate 19 to be received in the proximal end of the drive sleeve 21. In more detail, the prism 67 extends axially from the housing 61 of the dosage measurement device 60 such that the prism 67 extends through the space 71 of the button 18 and through the aperture 73 of the clutch plate 19. An end 67A of the prism 67 is received in the hollow centre of the drive sleeve 21.

The housing 61 of the dosage measurement device 60 comprises one or more attachment formations 74 that are configured to engage with corresponding attachment formations 75 on the button 18. In the present embodiment, the attachment formations 74 of the dosage measurement device 60 comprise projections 74 that engage with respective recesses 75 in the button 18 such that the dosage measurement device 60 can be clipped to the button 18. However, it should be recognised that in alternative embodiments (not shown) the attachment formations 74 are provided on a different component of the injection device 1.

In some embodiments, the engagement of the attachment formations 74, 75 is such that the dosage measurement device 60 cannot rotate relative to the button 18 when attached thereto.

In embodiments wherein the dosage measurement device 60 is to be releasably attachable to the injection device 1, the attachment formations 74, 75 may provide a clip-type arrangement that allows for easy removal of the dosage measurement device 60. Such an arrangement may be useful where the dosage measurement device 60 is to be used with disposable injection devices 1, since it allows the dosage measurement device 60 to be removed from an injection device 1 and reused. A removable dosage measurement device 60 also affords the user greater flexibility since the user is able to attach and remove the dosage measurement device 60 at will.

In some embodiments, the attachment formations 74, 75 may be configured to permanently attach the dosage measurement device 60 to the injection device 1, for example, using a "snap-fit". Alternatively, the dosage measurement device 60 may be permanently attached in other ways, for example, through bonding. Such permanent attachment may be useful where the injection device 1 is reusable. The number and/or positions of the attachment formations 74, 75 may be configured so that the dosage measurement device 60 can only be attached to the injection device 1 in one particular orientation relative to the injection device 1.

In some embodiments, the radially-inwardly facing inner surface 21A of the drive sleeve 21 comprises one or more detection elements 76 that are detectable by the sensor 66. In the present embodiment, the inner surface 21A of the drive sleeve 21 comprises a plurality of detection elements 76. The detection elements 76 are arranged in an array that subtends circumferentially about the central axis of the drive sleeve 21.

In the particular example shown in FIG. 11, twelve detection elements 76 are provided. The twelve detection elements 76 and the gaps between them have widths selected to provide "edges" 77, to correspond to dose increments up to a maximum dose of, in one particular example, twenty-four units shown on the number sleeve 4.

The detection elements 76 comprise a material that has a reflectivity that differs from the material of the inner surface 21A of the drive sleeve 21. In one embodiment, the detection elements 76 have a higher reflectivity than the inner surface 21A of the drive sleeve 21. In an alternative embodiment, the detection elements 76 have a lower reflectivity than the inner surface 21A of the drive sleeve 21. The detection elements 76 may be rectangular. The detection elements 76 may be adhered to the inner surface 21A of the drive sleeve 21.

In alternative embodiments (not shown), the detection elements 76 comprise apertures in the drive sleeve 21. Alternatively, the detection elements 76 may comprise castellations (not shown) that are moulded onto one end of the drive sleeve 21. One end of the drive sleeve 21 is provided with castellations that may act as light barriers for light emitted by the light source 66A. The castellations may be formed using a material that has a reflectivity that differs from that of an inner surface 21A of the drive sleeve 21.

In some embodiments, the number sleeve 4 is arranged to rotate helically along one direction as a dose is dialled into the injection device 1 using the dose dial 2 and also to rotate helically in an opposite direction during delivery of a medicament dose by the injection device 1.

The prism 67 is configured such that, when the dosage measurement device 60 is attached to the injection device 1, light emitted from the light source 66A is transmitted axially along the length of the prism 67 and is then reflected off an angled end surface 67A such that the reflected light has a radial component. Thus, the light (depicted by arrow I' in FIG. 11) is transmitted from the prism 67 in a generally radial direction, although the light may still have an axial component such that the light exits the prism 67 at an angle between the radial and axial direction. The light transmitted from the prism 67 impinges on the inner surface 21A of the drive sleeve 21 and/or on one of the detection elements 76, depending on the rotational position of the drive sleeve 21.

In other words, the light emitted by the light source 66A will be reflected by the inner surface 21A of the drive sleeve 21 and/or one of the detection elements 76, depending on the rotational position of the drive sleeve 21.

In some embodiments, prism 67 is configured such that the light is reflected by the principle of total internal reflection. That is, the refractive index is lower in the air than in the material of the prism 67 and the incident angle of the light reaching the end surface 67A of the prism 67 is less than the critical angle such that the light is entirely reflected. However, it should be recognised that this configuration is not essential to the functioning of the disclosure. For instance, the sensor unit 65 would still function if a portion of the light passed through the end surface 67A of the prism 67.

In some embodiments (not shown), the light guide 67 may comprise a reflective element (not shown), for example, a mirror, that is angled to reflect the light such that the light is directed radially towards the inner surface 21A of the drive sleeve 21.

In the present embodiment, once the light is reflected by the inner surface 21A of the drive sleeve 21 or by one of the detection elements 76, the reflected light will travel back towards the prism 76 and will enter the prism 76, travelling in a generally radial direction. The light will then again be reflected from the end surface 67A of the prism 67 such that the light travels axially, this time in the proximal direction, through the prism 67 until the light reaches the sensor 66 wherein the light is detected by the light detector 66B.

Since the reflectivity of the detection elements 76 differs from that of the inner surface 21A of the drive sleeve 21, the amount of light detected by the light detector 66B will depend on how much of the light is reflected by a detection element 76. In certain embodiments, the sensor 66 may be arranged to emit and/or detect only light with particular polarisation characteristics, in order to mitigate effects of stray light.

Figure 15:
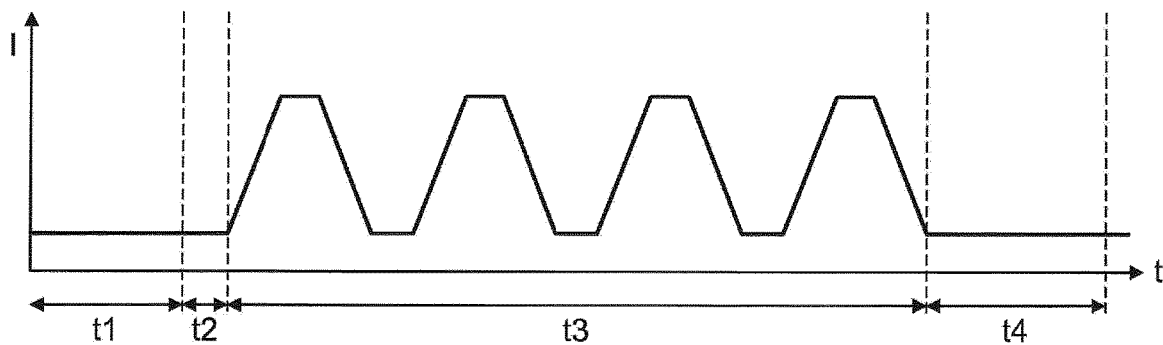
FIG. 15 is a graph showing an intensity of light received by a sensor arrangement in the data measurement system of FIG. 1.
Figure 16:
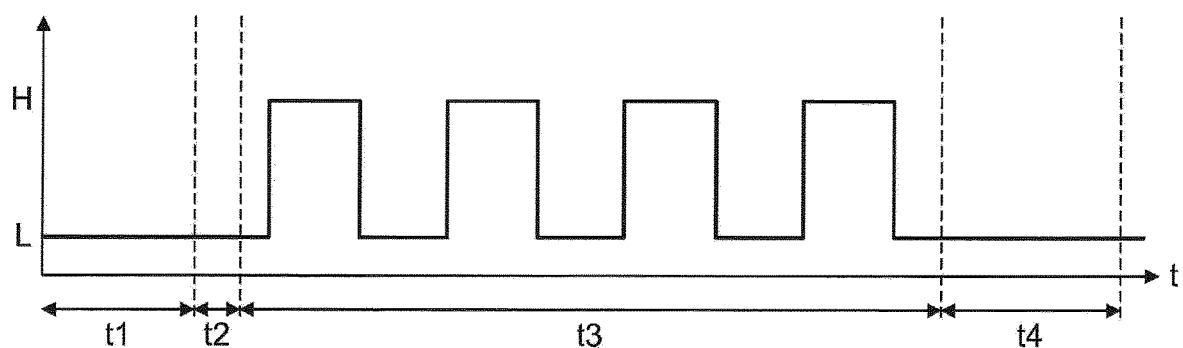
FIG. 16 is a graph showing an output of the sensor arrangement based on the received light intensities shown in FIG. 15.

FIG. 15 is a graph showing changes in the intensity of light received by the light detector 66B during programming and delivery of a medicament dose, while FIG. 16 is a graph showing an output signal that may be generated by the sensor 66 of this embodiment.

As noted above, while a dose is being programmed into the injection device 1, during time period t1 in FIGS. 7 and 8, the drive sleeve 21 does not rotate relative to the sensor unit 65. Therefore, in this particular embodiment, since the drive sleeve 21 does not rotate, the amount of light reflected back towards the light detector 66B should remain substantially constant while the dose is being programmed. The amount of reflected light should also remain substantially constant between the completion of dosage programming and the start of the injection, shown as time period t2 in FIG. 7, since the drive sleeve 21 and sensor unit 65 are not being rotated by a user.

The output of the sensor 66, shown in FIG. 8, is therefore substantially constant during time periods t1 and t2. The actual level of the output during time periods t1 and t2 will depend on the proportion of light emitted by the light source 66A that is reflected by a detection element 76 and the proportion that is reflected by the inner surface 21A of the drive sleeve 21.

During the delivery of the medicament, shown as time period t3 in FIGS. 7 and 8, the drive sleeve 21 rotates relative to the button 18. Therefore, the drive sleeve 21 also rotates relative to the sensor unit 65 during the delivery of the medicament, the sensor unit 65 being attached to the button 18.

During time period t3, the detection elements 76 of the number sleeve 70 will move across the beam of light transmitted from the prism 67 as the drive sleeve 21 rotates relative to the sensor unit 65, and the intensity of light received by the light detector 66B will vary accordingly, as shown in FIG. 7. In this particular example, the material of the detection elements 76 is more reflective than the inner surface 21A of the drive sleeve 21, and so the highest intensity levels shown in FIG. 7 correspond to positions wherein the highest proportion of the light is reflected by a detection element 76.

The output of the light detector 66B during time period t3 will switch between a high and a low level, based on the received light intensity, as shown in FIG. 8. Since the edges of the detection elements 76 correspond to increments in the medicament dosage, the processor 63 can determine an amount of medication delivered by the injection device based on the number of transitions between the high level and the low level in the output of the sensor 66.

The length of time period t3 will depend on the administered dosage and also on when the medicament delivery is deemed to be complete. When the medicament delivery is complete, the drive sleeve 21 will cease to rotate relative to the button 18 and the dosage measurement device 60, and the signal from the sensor 66 will stay at a substantially constant level.

In some embodiments, the processor 63 is arranged to monitor the time period that has elapsed from the last transition or the last pulse in the output of the sensor 66. When the elapsed time period reaches a predetermined threshold t4, the medicament delivery is considered to have been completed and the processor 63 proceeds with determining the medicament dose delivered to the user, based on the number of detected transitions in the output of the sensor 66 during time period t3. In the particular example shown in FIGS. 7 and 8, there are eight transitions. Since the transitions correspond to the edges of the detection elements 76 which, in turn, correspond to the dosage increments in this particular embodiment, the determined medicament dose is 8 units.

The processor 63 then stores the determined medicament dose in main memory 64B. The processor 63 may also store time stamp information, to provide a log recording delivery of medicament to the user. The processor 63 may then power down the dosage measurement device 60, in order to conserve battery power.

When the dosage measurement device 60 is powered on again, by a user activating the power switch 69, the processor 63 may control the display 62 to show the determined medicament dose information, to aid the memory of the user. Optionally, the processor 63 may monitor an elapsed time since the determined medicament dose was delivered and control the display to show that elapsed time information too. For example, the processor 63 may cause the display 62 to switch periodically between displaying the determined medicament dosage information and the elapsed time.

The processor 63 may also transmit the determined medicament dosage and, where determined, the time stamp information to another device, such as a computer (not shown). As noted above, the output 68 may be configured to transmit the information using a wireless communications link. Alternatively, the dosage measurement device 60 may be connected to the computer (not shown) using a wired connection (not shown) to allow the information to be uploaded to the computer. The processor 63 may be configured to transmit the information to the computer periodically. In some embodiments, the display 62 may be omitted. In some embodiments, the dosage measurement system 62 may be used to monitor compliance with a particular dosage regime.

The specific embodiments described in detail above are intended merely as examples of how the present disclosure may be implemented. Many variations in the configuration of the dosage measurement device 60 and/or the injection device 1 may be conceived. For example, it is not necessary that the detection elements 76 provided on the drive sleeve 21 are in the form of reflective material, nor is it necessary for the widths of the detection elements 76 and the gaps between them to correspond precisely to individual dosage increments, as in the above embodiment.

While the above described embodiment utilises an optical sensor 66, other types of sensors may be used as well as, or instead of, optical sensors. For example, the sensor may include a magnetic sensor, such as a Hall effect sensor. In such an example, the detection elements may comprise one or more magnets may be mounted on the drive sleeve 21, so that rotation of the drive sleeve 21 relative to the sensor unit 65 results in a varying magnetic field. In another example, a capacitive sensor may be used, wherein the detection elements may comprise elements provided on the drive sleeve that affect the capacitance between two plates provided in the sensor unit. In other examples, mechanical sensors, with mechanical switches and/or tracks, may be used to detect the relative movement of the drive sleeve 21 relative to the sensor unit. While the embodiment shown in FIGS. 1 to 14 includes only one sensor, other embodiments may be devised in which the sensor arrangement includes multiple sensors of one or more types.

Figure 17:
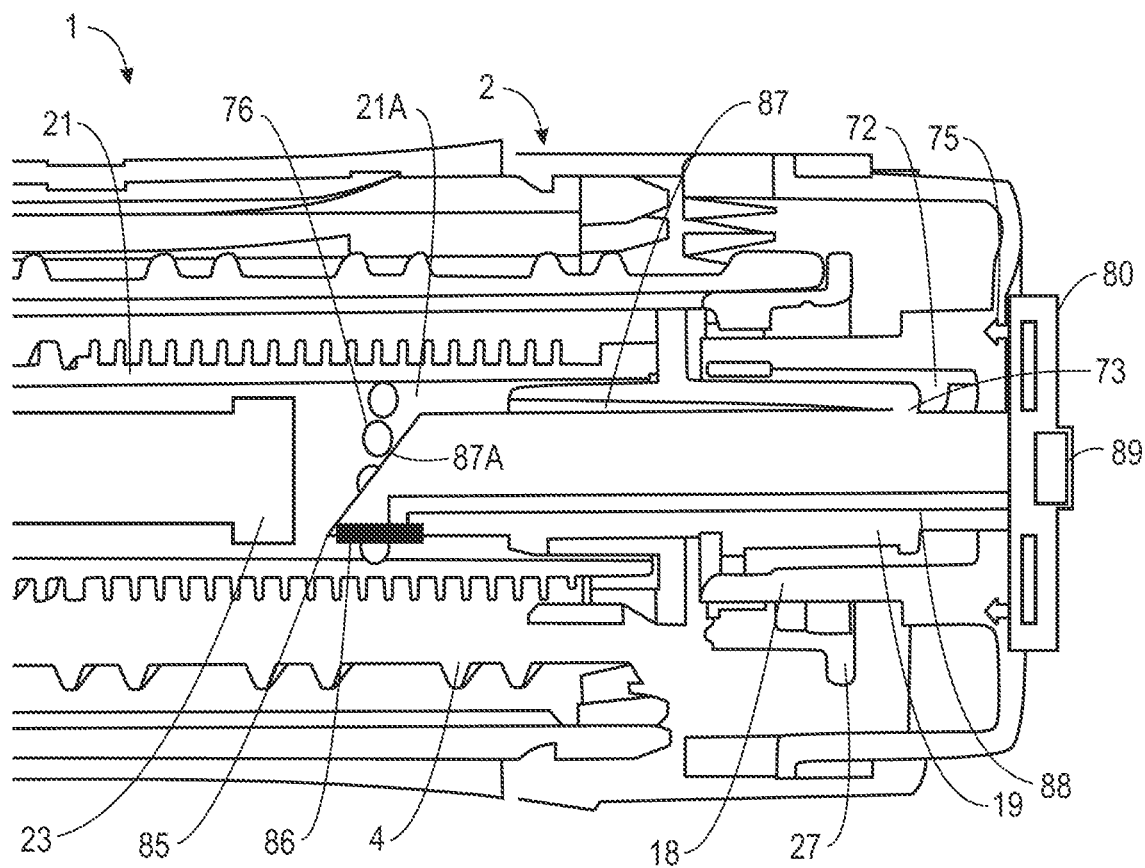
FIG. 17 is a cross-sectional side view of part of a medicament delivery system according to a second embodiment of the disclosure; and, FIG. 18 is a schematic cross-sectional side view of part of a medicament delivery system according to a third embodiment of the disclosure.

Referring now to FIG. 17, a medicament delivery system according to a second embodiment of the disclosure is shown. The medicament delivery system is similar to the measurement delivery system described above in reference to the first embodiment of the disclosure, with like features retaining the same reference numerals. The medicament delivery system comprises a medicament delivery device 1 and a dosage measurement system 80.

The medicament delivery device 1 is in the form of an injection device 1. The dosage measurement system 80 comprises a dosage measurement device 80 that is attached to a proximal end of the injection device 1. The dosage measurement device 80 comprises a housing 81, a processor (not shown), computer readable memory media (not shown), a power switch 89, a battery (not shown), and an output (not shown).

A difference between the dosage measurement system 60 of the first embodiment and the dosage measurement system 80 of the second embodiment is that the sensor unit 65 is omitted and is replaced by an alternative sensor unit 85. The sensor unit 85 comprises a sensor 86, which in the present embodiment is an optical sensor 86 having a light source (not shown) and a light detector (not shown). However, the light guide 86 of the sensor unit 65 of the first embodiment is omitted and instead the sensor 86 is located on a support member 87.

The support member 87 extends from the housing 81 such that when the dosage measurement device 80 is attached to the injection device 1, the support member 87 extends axially in the distal direction such that an end 87A of the support member 87 is located within the drive sleeve 21. The sensor 86 is mounted on, or proximate to, said 87A such that the sensor 86 is directed towards the inner surface 21A of the drive sleeve 21 and the detection elements 76 located thereon. More specifically, the sensor 86 is arranged such that light emitted by the light source (not shown) irradiates the inner surface 21A of the drive sleeve and/or one of the detection elements 76, depending on the rotational position of the drive sleeve 21, and is reflected thereby. The reflected light travels back towards the sensor 86 and is detected by the light detector (not shown).

The sensor 86 is connected to the processor (not shown) by one or more conductive elements 88, for example, tracks or wires, which extend from the sensor 86 to the housing 81. The conductive elements 88 may be adhered to or embedded in the support member 87.

As before, since the reflectivity of the detection elements 76 differs from that of the inner surface 21A of the drive sleeve 21, the amount of light detected by the light detector (not shown) of the sensor 86 will depend on how much of the light is reflected by a detection element 76 and thus will depend on the rotational position of the drive sleeve 21. Therefore, the processor (not shown) is able to determine a dosage dispensed from the injection device 1 based on the output of the sensor unit 85, which measures the rotation of the drive sleeve 21.

In the above described embodiments, the button 18 includes an aperture 71 to allow for the dosage measurement device 60 to be inserted into the space 72 of the button 18. However, it should be recognised that in alternative embodiments (not shown) the aperture 71 is omitted. For example, the dosage measurement system 60 may be integrated into the injection device 1 such that the dosage measurement system 60 is permanently received in the space 72.

In other embodiments, the dosage measurement system 60 is removably attached or permanently fixed to a part of the injection device 1 other than the button 18, for instance, the housing 3.

In the above described embodiments the attachment formations 74, 75 are in the form of projections 74 on the housing 61 of the dosage measurement device 60 that are received in respective recesses 75 in the button 18. However, it should be recognised that other types of engaging attachment formations or attachment methods may be used. In one alternative embodiment (not shown), the attachment formations are in the form of projections 74 on the button 18 that are received in respective recesses in the housing 61 of the dosage measurement device 60. Alternatively, the dosage measurement system 60 may be bonded to the injection device 1. In one embodiment (not shown), the dosage measurement system 60 is permanently integrated with the injection device 1. For instance, the dosage measurement system 60 may be integrated with the injection device 1 during assembly of the injection device 1. In one embodiment, the housing 61 of the dosage measurement system 60 is omitted and instead one or more components of the injection device 1, for example, the button 18, drive sleeve 21 and/or housing 3, contain the components of the dosage measurement system 60.

In the above described embodiments, the detection elements 76 are provided on the inner surface 21A of the drive sleeve 21 and the sensor 66, 86 is directed towards the inner surface 21A to detect the detection elements 76. In alternative embodiments (not shown), the detection elements may instead be provided on the lead screw 23, for example, on a proximally-facing end surface of the lead screw 23, and the sensor may be directed towards the detection elements. The sensor 66, 86 detects rotation of the lead screw 23 and the processor determines the dosage dispensed from the medicament reservoir based on the measured rotation of the lead screw.

Figure 18:
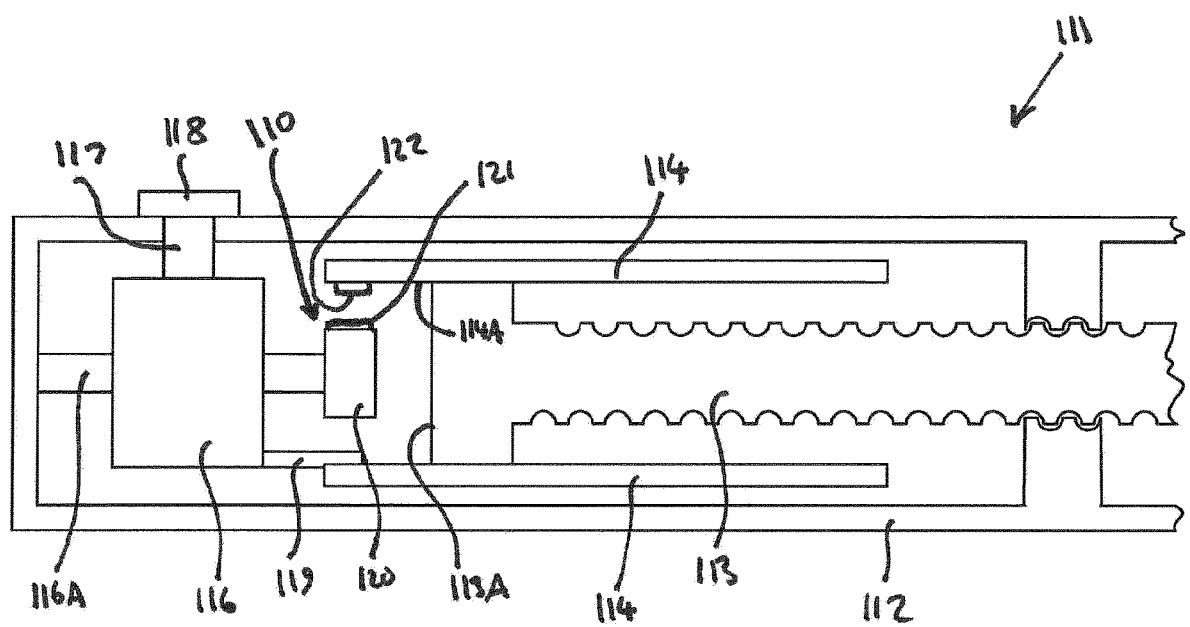

Referring now to FIG. 18, a schematic view of a medicament delivery system according to a third embodiment of the disclosure is shown. The medicament delivery system comprises a medicament delivery device 111 and a dosage measurement system 110.

The medicament delivery device 111 is in the form of an injection device 111. The medicament delivery device 111 comprises a housing 112 that contains a medicament reservoir (not shown), plunger (not shown), lead screw 113, drive sleeve 114 and drive unit 115.

The drive unit 115 is configured to rotate the drive sleeve 114 relative to the housing 112. The drive sleeve 114 engages with the lead screw 113 such that rotation of the drive sleeve 114 causes rotation of the lead screw 113. The lead screw 113 and drive sleeve 114 may engage via, for example, a threaded interface (not shown).

The lead screw 113 also engages with the housing 112 such that rotation of the lead screw 113 relative to the housing 112 causes axial displacement of the lead screw 113 relative to the housing 112 such that the plunger is moved within the medicament reservoir to dispense medicament therefrom. Thus, operation of the drive unit 115 causes rotation of the drive sleeve 114 such that the lead screw 113 is moved axially relative to the housing 112 to dispense medicament from the medicament reservoir.

The drive unit 115 comprises a biasing member 116 and a locking mechanism 117 that is coupled to an actuator 118. The biasing member 116 is configured to bias the drive sleeve 114 to rotate relative to the housing 112. The biasing member 116 is mounted to an axle 116A such that a first end of the biasing member 116 is connected to the axle 116A. A second end of the biasing member 116 is coupled to the drive sleeve 114 by a connecting member 119. In the present embodiment, the connecting member 119 is fixed relative to the second end of the biasing member 116 and is received in a groove (not shown) in the inside surface of the drive sleeve 114 such that the connecting member 119 is rotationally fixed relative to the drive sleeve 114.

The locking mechanism 117 initially prevents the biasing member 116 from rotating the drive sleeve 114 relative to the housing 112. The locking mechanism 117 is coupled to the actuator 118 such that the actuator 118 is operable to release the drive sleeve 114. The locking mechanism 117 may comprise, for example, a locking pin (not shown) that initially engages the second end of the biasing member 116 to prevent movement of the biasing member 116 relative to the housing 112. Actuation of the actuator 118 by the user may move the locking pin out of engagement with the second end of the biasing member 116. However, the locking mechanism may have a different arrangement, for example, in one embodiment (not shown) comprising an electromagnetic latch that is operated to release the biasing member.

To operate the medicament delivery device 111, the user presses the actuator 118 such that the locking mechanism 117 releases the biasing member 116 and thus the drive sleeve 114 is rotated relative to the housing 112. This causes the lead screw 113 to be rotated relative to the housing 112 and moved axially relative to the housing 112 such that the plunger (not shown) is moved axially within the medicament reservoir and thus medicament is dispensed therefrom. The medicament reservoir may be fluidly connected to, for example, a needle, for delivery of the medicament to a patient.

The dosage measurement system 110 comprises a sensor unit 120 having a sensor 121 and a processor (not shown). In the present embodiment the sensor 121 is an optical sensor 121 having a light source (not shown) and a light detector (not shown). In the present embodiment, the sensor unit 120 is mounted to the axle 116A that supports the biasing member 116. However, it should be recognised that in alternative embodiments (not shown) the sensor unit 120 is mounted to a different part of the medicament delivery device 111, for example, the housing 112.

The sensor 121 is directed towards the inner surface 114A of the drive sleeve 114 such that the sensor 121 detects the presence of detection elements 122 mounted on the inner surface 114A. More specifically, the sensor 121 is arranged such that light emitted by the light source (not shown) irradiates the inner surface 114A of the drive sleeve 114 and/or one of the detection elements 122, depending on the rotational position of the drive sleeve 114, and is reflected thereby. The reflected light travels back towards the sensor 121 and is detected by the light detector (not shown). In some embodiments (not shown), the sensor unit 120 further comprises a transmission member (not shown), such as a light guide, that transmits a signal from the sensor 121 towards the inner surface 114A of the drive sleeve 114.

The sensor 120 is connected to the processor (not shown). As described above in reference to the first and second embodiments, since the reflectivity of the detection elements 122 differs from that of the inner surface 114A of the drive sleeve 114, the amount of light detected by the light detector (not shown) of the sensor 120 will depend on how much of the light is reflected by a detection element 122 and thus will depend on the rotational position of the drive sleeve 114. Therefore, the processor (not shown) is able to determine a dosage dispensed from the injection device 111 based on the output of the sensor unit 120, which measures the rotation of the drive sleeve 114.

In an alternative embodiment (not shown), the sensor 121 is instead directed towards an end surface 113A of the lead screw 113 such that such that the sensor 121 detects the presence of detection elements (not shown) provided at the end surface 113A. In such an alternative embodiment, the sensor 121 may be arranged such that light emitted by the light source (not shown) irradiates the inner surface 113A of the lead screw 113 and/or one of the detection elements, depending on the rotational position of the lead screw 113, and is reflected thereby. The reflected light travels back towards the sensor 121 and is detected by the light detector (not shown). Since the reflectivity of the detection elements differs from that of the end surface 113A of the lead screw 113, the amount of light detected by the light detector (not shown) of the sensor 120 will depend on how much of the light is reflected by a detection element and thus will depend on the rotational position of the lead screw 113. Therefore, the processor (not shown) is able to determine a dosage dispensed from the injection device 111 based on the output of the sensor unit 120, which measures the rotation of the lead screw 113.

In the present embodiment, the biasing member 116 is in the form of a torsion spring 116. However, it should be recognised that other types of biasing member are intended to fall within the scope of the disclosure. In yet further embodiments (not shown), the biasing member is omitted and instead the drive unit comprises an electric motor that is operated to rotate the drive sleeve and thus dispense the medicament from the medicament reservoir. Alternatively, the drive unit may comprise a component that is manually rotated by the user to rotate the drive sleeve to dispense the medicament.

In some embodiments (not shown), the dosage measurement system 60, 80, 110 comprises a first part and a second part that is attachable to the first part. The second part may be releasably attachable to the first part. The first part of the dosage measurement device 60, 80, 110 may comprise one or more attachment formations (not shown) that are configured to engage with corresponding attachment formations (not shown) on the second part. The attachment formations of the first part or second part may comprise projections that engage with respective recesses in the other of the first and second part such that the second part can be clipped to the first part. However, it should be recognised that in alternative embodiments (not shown) the second part is attached to the first part via a different arrangement, for example, being received in a recess in the first part such that the first and second parts are held together via friction. The first and second parts may comprise engaging elements, for example, rails that engage with grooves, which ensure a particular rotational orientation of the first part relative to the second part when the second part is attached to the first part.

The dosage measurement system 60, 80, 110 comprising first and second parts allows for the first part to be attached to, or integrated with, the injection device 1, 111 and for the second part to be removably attached to the first part. Therefore, the injection device 1, 111 and the first part can be disposed of and the second part can be reused by removing it from the first part and attaching it to the first part of a different injection device 1, 111. One or more of the battery, user interface, processor and sensor can be incorporated into the second part. Thus, these components, which are relatively expensive, can be reused with further injection devices by attaching the second part to the first part of said further injection devices. In one embodiment, the first part comprises a transmission member, for example, a light guide, that is fixed to the injection device 1, 111. The second part comprises a battery, processor and a sensor. The second part attaches to the first part such that the transmission member and sensor form a sensor unit, wherein the transmission member is able to transmit a signal emitted by the sensor towards the detection elements and also to transmit the reflected signal back towards the sensor. Once medicament delivery is complete, the second part is detached from the first part and the first part together with the medicament delivery device is disposed of. In another embodiment (not shown), the first part comprises a support member that is fixed to the injection device 1, 111 and a sensor that is provided on the support member. The second part comprises a battery and processor. The second part attaches to the first part such that the sensor is coupled to the processor and thus the processor is able to determine a dosage dispensed from the medicament reservoir based on the measured rotation of said at least one of the drive sleeve and lead screw. Once medicament delivery is complete, the second part is detached from the first part and the first part together with the medicament delivery device is disposed of.

In the above described embodiments the medicament delivery device 1, 111 comprises an injection device. The injection device may comprise a pen injection device and may comprise an autoinjector. However, it should be recognised that the medicament delivery system may comprise a different type of medicament delivery device. For example, the medicament delivery device may comprise a patch device that is attached to the injection site of a patient. The medicament delivery device may be a pump device.

While the embodiments above have been described in relation to collecting data from an insulin injector pen, it is noted that embodiments of the disclosure may be used for other purposes, such as monitoring of injections of other medicaments.

The terms "drug" or "medicament" are used herein to describe one or more pharmaceutically active compounds. As described below, a drug or medicament can include at least one small or large molecule, or combinations thereof, in various types of formulations, for the treatment of one or more diseases. Exemplary pharmaceutically active compounds may include small molecules; polypeptides, peptides and proteins (e.g., hormones, growth factors, antibodies, antibody fragments, and enzymes); carbohydrates and polysaccharides; and nucleic acids, double or single stranded DNA (including naked and cDNA), RNA, antisense nucleic acids such as antisense DNA and RNA, small interfering RNA (siRNA), ribozymes, genes, and oligonucleotides. Nucleic acids may be incorporated into molecular delivery systems such as vectors, plasmids, or liposomes. Mixtures of one or more of these drugs are also contemplated.

The term "medicament delivery device", which is also referred to hereinafter as "drug delivery device", shall encompass any type of device or system configured to dispense a drug into a human or animal body. Without limitation, a drug or medicament delivery device may be an injection device (e.g., syringe, pen injector, auto injector, large-volume device, pump, perfusion system, or other device configured for intraocular, subcutaneous, intramuscular, or intravascular delivery), skin patch (e.g., osmotic, chemical, micro-needle), inhaler (e.g., nasal or pulmonary), implantable (e.g., coated stent, capsule), or feeding systems for the gastro-intestinal tract. The presently described drugs may be particularly useful with injection devices that include a needle, e.g., a small gauge needle.

The drug or medicament may be contained in a primary package or "drug container" adapted for use with a drug delivery device. The drug container may be, e.g., a cartridge, syringe, reservoir, or other vessel configured to provide a suitable chamber for storage (e.g., short- or long-term storage) of one or more pharmaceutically active compounds. For example, in some instances, the chamber may be designed to store a drug for at least one day (e.g., 1 to at least 30 days). In some instances, the chamber may be designed to store a drug for about 1 month to about 2 years. Storage may occur at room temperature (e.g., about 20° C.), or refrigerated temperatures (e.g., from about −4° C. to about 4° C.). In some instances, the drug container may be or may include a dual-chamber cartridge configured to store two or more components of a drug formulation (e.g., a drug and a diluent, or two different types of drugs) separately, one in each chamber. In such instances, the two chambers of the dual-chamber cartridge may be configured to allow mixing between the two or more components of the drug or medicament prior to and/or during dispensing into the human or animal body. For example, the two chambers may be configured such that they are in fluid communication with each other (e.g., by way of a conduit between the two chambers) and allow mixing of the two components when desired by a user prior to dispensing. Alternatively or in addition, the two chambers may be configured to allow mixing as the components are being dispensed into the human or animal body.

The drug delivery devices and drugs described herein can be used for the treatment and/or prophylaxis of many different types of disorders. Exemplary disorders include, e.g., diabetes mellitus or complications associated with diabetes mellitus such as diabetic retinopathy, thromboembolism disorders such as deep vein or pulmonary thromboembolism. Further exemplary disorders are acute coronary syndrome (ACS), angina, myocardial infarction, cancer, macular degeneration, inflammation, hay fever, atherosclerosis and/or rheumatoid arthritis.

Exemplary drugs for the treatment and/or prophylaxis of diabetes mellitus or complications associated with diabetes mellitus include an insulin, e.g., human insulin, or a human insulin analogue or derivative, a glucagon-like peptide (GLP-1), GLP-1 analogues or GLP-1 receptor agonists, or an analogue or derivative thereof, a dipeptidyl peptidase-4 (DPP4) inhibitor, or a pharmaceutically acceptable salt or solvate thereof, or any mixture thereof. As used herein, the term "derivative" refers to any substance which is sufficiently structurally similar to the original substance so as to have substantially similar functionality or activity (e.g., therapeutic effectiveness).

Exemplary insulin analogues are Gly(A21), Arg(B31), Arg(B32) human insulin (insulin glargine); Lys(B3), Glu(B29) human insulin; Lys(B28), Pro(B29) human insulin; Asp(B28) human insulin; human insulin, wherein proline in position B28 is replaced by Asp, Lys, Leu, Val or Ala and wherein in position B29 Lys may be replaced by Pro; Ala(B26) human insulin; Des(B28-B30) human insulin; Des(B27) human insulin and Des(B30) human insulin.

Exemplary insulin derivatives are, for example, B29-N-myristoyl-des(B30) human insulin; B29-N-palmitoyl-des(B30) human insulin; B29-N-myristoyl human insulin; B29-N-palmitoyl human insulin; B28-N-myristoyl LysB28ProB29 human insulin; B28-N-palmitoyl-LysB28ProB29 human insulin; B30-N-myristoyl-ThrB29LysB30 human insulin; B30-N-palmitoyl-ThrB29LysB30 human insulin; B29-N—(N-palmitoyl-gamma-glutamyl)-des(B30) human insulin; B29-N—(N-lithocholyl-gamma-glutamyl)-des(B30) human insulin; B29-N-(ω-carboxyheptadecanoyl)-des(B30) human insulin and B29-N-(ω-carboxyhepta¬decanoyl) human insulin.

Exemplary GLP-1, GLP-1 analogues and GLP-1 receptor agonists are, for example: Lixisenatide/AVE0010/ZP10/Lyxumia, Exenatide/Exendin-4/Byetta/Bydureon/ITCA 650/AC-2993 (a 39 amino acid peptide which is produced by the salivary glands of the Gila monster), Liraglutide/Victoza, Semaglutide, Taspoglutide, Syncria/Albiglutide, Dulaglutide, rExendin-4, CJC-1134-PC, PB-1023, TTP-054, Langlenatide/HM-11260C, CM-3, GLP-1 Eligen, ORMD-0901, NN-9924, NN-9926, NN-9927, Nodexen, Viador-GLP-1, CVX-096, ZYOG-1, ZYD-1, GSK-2374697, DA-3091, MAR-701, MAR709, ZP-2929, ZP-3022, TT-401, BHM-034. MOD-6030, CAM-2036, DA-15864, ARI-2651, ARI-2255, Exenatide-XTEN and Glucagon-Xten.

An exemplary oligonucleotide is, for example: mipomersen/Kynamro, a cholesterol-reducing antisense therapeutic for the treatment of familial hypercholesterolemia.

Exemplary DPP4 inhibitors are Vildagliptin, Sitagliptin, Denagliptin, Saxagliptin, Berberine.

Exemplary hormones include hypophysis hormones or hypothalamus hormones or regulatory active peptides and their antagonists, such as Gonadotropine (Follitropin, Lutropin, Choriongonadotropin, Menotropin), Somatropine (Somatropin), Desmopressin, Terlipressin, Gonadorelin, Triptorelin, Leuprorelin, Buserelin, Nafarelin, and Goserelin.

Exemplary polysaccharides include a glucosaminoglycane, a hyaluronic acid, a heparin, a low molecular weight heparin or an ultra-low molecular weight heparin or a derivative thereof, or a sulphated polysaccharide, e.g. a poly-sulphated form of the above-mentioned polysaccharides, and/or a pharmaceutically acceptable salt thereof. An example of a pharmaceutically acceptable salt of a poly-sulphated low molecular weight heparin is enoxaparin sodium. An example of a hyaluronic acid derivative is Hylan G-F 20/Synvisc, a sodium hyaluronate.

The term "antibody", as used herein, refers to an immunoglobulin molecule or an antigen-binding portion thereof. Examples of antigen-binding portions of immunoglobulin molecules include F(ab) and F(ab')2 fragments, which retain the ability to bind antigen. The antibody can be polyclonal, monoclonal, recombinant, chimeric, de-immunized or humanized, fully human, non-human, (e.g., murine), or single chain antibody. In some embodiments, the antibody has effector function and can fix complement. In some embodiments, the antibody has reduced or no ability to bind an Fc receptor. For example, the antibody can be an isotype or subtype, an antibody fragment or mutant, which does not support binding to an Fc receptor, e.g., it has a mutagenized or deleted Fc receptor binding region.

The terms "fragment" or "antibody fragment" refer to a polypeptide derived from an antibody polypeptide molecule (e.g., an antibody heavy and/or light chain polypeptide) that does not comprise a full-length antibody polypeptide, but that still comprises at least a portion of a full-length antibody polypeptide that is capable of binding to an antigen. Antibody fragments can comprise a cleaved portion of a full length antibody polypeptide, although the term is not limited to such cleaved fragments. Antibody fragments that are useful in the present disclosure include, for example, Fab fragments, F(ab')2 fragments, scFv (single-chain Fv) fragments, linear antibodies, monospecific or multispecific antibody fragments such as bispecific, trispecific, and multispecific antibodies (e.g., diabodies, triabodies, tetrabodies), minibodies, chelating recombinant antibodies, tribodies or bibodies, intrabodies, nanobodies, small modular immunopharmaceuticals (SMIP), binding-domain immunoglobulin fusion proteins, camelized antibodies, and VHH containing antibodies. Additional examples of antigen-binding antibody fragments are known in the art.

The terms "Complementarity-determining region" or "CDR" refer to short polypeptide sequences within the variable region of both heavy and light chain polypeptides that are primarily responsible for mediating specific antigen recognition. The term "framework region" refers to amino acid sequences within the variable region of both heavy and light chain polypeptides that are not CDR sequences, and are primarily responsible for maintaining correct positioning of the CDR sequences to permit antigen binding. Although the framework regions themselves typically do not directly participate in antigen binding, as is known in the art, certain residues within the framework regions of certain antibodies can directly participate in antigen binding or can affect the ability of one or more amino acids in CDRs to interact with antigen.

Exemplary antibodies are anti PCSK-9 mAb (e.g., Alirocumab), anti IL-6 mAb (e.g., Sarilumab), and anti IL-4 mAb (e.g., Dupilumab).

The compounds described herein may be used in pharmaceutical formulations comprising (a) the compound(s) or pharmaceutically acceptable salts thereof, and (b) a pharmaceutically acceptable carrier. The compounds may also be used in pharmaceutical formulations that include one or more other active pharmaceutical ingredients or in pharmaceutical formulations in which the present compound or a pharmaceutically acceptable salt thereof is the only active ingredient. Accordingly, the pharmaceutical formulations of the present disclosure encompass any formulation made by admixing a compound described herein and a pharmaceutically acceptable carrier.

Pharmaceutically acceptable salts of any drug described herein are also contemplated for use in drug delivery devices. Pharmaceutically acceptable salts are for example acid addition salts and basic salts. Acid addition salts are e.g. HCl or HBr salts. Basic salts are e.g. salts having a cation selected from an alkali or alkaline earth metal, e.g. Na+, or K+, or Ca2+, or an ammonium ion N+(R1)(R2)(R3)(R4), wherein R1 to R4 independently of each other mean: hydrogen, an optionally substituted C1 C6-alkyl group, an optionally substituted C2-C6-alkenyl group, an optionally substituted C6-C10-aryl group, or an optionally substituted C6-C10-heteroaryl group. Further examples of pharmaceutically acceptable salts are known to those of skill in the arts.

Pharmaceutically acceptable solvates are for example hydrates or alkanolates such as methanolates or ethanolates.

Those of skill in the art will understand that modifications (additions and/or removals) of various components of the substances, formulations, apparatuses, methods, systems and embodiments described herein may be made without departing from the full scope and spirit of the present disclosure, which encompass such modifications and any and all equivalents thereof.

The invention claimed is:

1. A medicament delivery system comprising:
   a medicament delivery device comprising:
     a medicament reservoir,
     a lead screw, and
     a drive sleeve that is rotatable to axially displace the lead screw relative to the drive sleeve to dispense a medicament from the medicament reservoir, wherein the drive sleeve is prevented from rotating during dose setting; and
   a dosage measurement system comprising:
     a sensor unit configured to measure a rotation of at least one of the drive sleeve and the lead screw of the medicament delivery device, wherein the sensor unit is further configured to be at least partially located within the drive sleeve of the medicament delivery device; and
     a processor configured to determine a dosage dispensed from the medicament reservoir of the medicament delivery device based on a measured rotation of at least one of the drive sleeve and the lead screw.

2. A medicament delivery system according to claim 1, wherein the medicament reservoir contains the medicament.

3. A medicament delivery system according to claim 1, wherein the sensor unit is configured to transmit a signal such that the signal is reflected from at least one of the drive sleeve and the lead screw of the medicament delivery device, and wherein the sensor unit is further configured to receive the signal that is reflected.

4. A medicament delivery system according to claim 3, wherein the sensor unit comprises a transmission member through which the signal is transmitted.

5. A medicament delivery system according to claim 4, wherein the transmission member extends into the drive sleeve of the medicament delivery device.

6. A medicament delivery system according to claim 4, wherein the dosage measurement system comprises a first part configured to be fixed to the medicament delivery device and a second part that is removably attachable to the first part.

7. A medicament delivery system according to claim 6, wherein the first part comprises the transmission member.

8. A medicament delivery system according to claim 1, wherein the sensor unit is configured to transmit a signal that travels within the drive sleeve of the medicament delivery device and that is reflected from at least one of the drive sleeve and the lead screw.

9. A medicament delivery system according to claim 8, wherein the sensor unit is configured such that the signal is reflected from a radially-inwardly facing surface of the drive sleeve of the medicament delivery device.

10. A medicament delivery system according to claim 1, wherein the sensor unit is configured to detect one or more detection elements of at least one of the drive sleeve and the lead screw.

11. A medicament delivery system according to claim 1, wherein the sensor unit is integrated with the medicament delivery device.

12. A medicament delivery system according to claim 1, wherein the sensor unit is removably attachable to the medicament delivery device.

13. A medicament delivery system according to claim 1, wherein the medicament delivery device comprises an actuator that is actuatable by a user to dispense medicament, and wherein the sensor unit is configured to be mounted to the actuator.

14. A medicament delivery system according to claim 13, wherein the actuator comprises a space, and wherein the sensor unit is configured to be at least partially received in the space.

15. A medicament delivery system according to claim 1, wherein the sensor unit is configured to measure rotation of the drive sleeve of the medicament delivery device, and wherein the processor is configured to determine a dosage dispensed from the medicament reservoir of the medicament delivery device based on a measured rotation of the drive sleeve.

16. A medicament delivery system according to claim 4, wherein the transmission member comprises a light guide.

17. A medicament delivery system according to claim 6, wherein the second part comprises the processor.

18. A method of determining a dosage of a medicament dispensed from a medicament delivery device by using a medicament delivery system, wherein the medicament delivery system comprises:

the medicament delivery device, wherein the medicament delivery device comprises:
  a medicament reservoir,
  a lead screw, and
  a drive sleeve that is rotatable to axially displace the lead screw relative to the drive sleeve to dispense the medicament from the medicament reservoir, wherein the drive sleeve is prevented from rotating during dose setting, and
a dosage measurement system comprising:
  a sensor unit configured to measure a rotation of at least one of the drive sleeve and the lead screw of the medicament delivery device, wherein the sensor unit is further configured to be at least partially located within the drive sleeve of the medicament delivery device, and
  a processor configured to determine a dosage dispensed from the medicament reservoir of the medicament delivery device based on a measured rotation of at least one of the drive sleeve and the lead screw,
and wherein the method comprises:
measuring a rotation of at least one of the drive sleeve and the lead screw of the medicament delivery device while the medicament is dispensed from the medicament reservoir; and
determining the dosage dispensed from the medicament reservoir based on the rotation measured of at least one of the drive sleeve and the lead screw.

\* \* \* \* \*